(12) United States Patent
Brinkmann et al.

(10) Patent No.: US 9,890,204 B2
(45) Date of Patent: Feb. 13, 2018

(54) TRIVALENT, BISPECIFIC ANTIBODIES

(75) Inventors: Ulrich Brinkmann, Weilheim (DE);
Rebecca Croasdale, Antdorf (DE);
Eike Hoffmann, Seefeld (DE);
Christian Klein, Bonstetten (CH);
Ekkehard Moessner, Kreuzlingen (CH); Juergen Michael Schanzer, Traunstein (DE); Claudio Sustmann, Munich (DE); Pablo Umana, Zurich (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 13/568,224

(22) Filed: Aug. 7, 2012

(65) Prior Publication Data

US 2013/0022601 A1    Jan. 24, 2013

Related U.S. Application Data

(63) Continuation of application No. 12/752,216, filed on Apr. 1, 2010, now abandoned.

(30) Foreign Application Priority Data

Apr. 7, 2009    (EP) .................... 09005108

(51) Int. Cl.
*C07K 16/00* (2006.01)
*C07K 16/28* (2006.01)
*C07K 16/32* (2006.01)

(52) U.S. Cl.
CPC .......... *C07K 16/00* (2013.01); *C07K 16/2863* (2013.01); *C07K 16/32* (2013.01); *C07K 2317/24* (2013.01); *C07K 2317/31* (2013.01); *C07K 2317/565* (2013.01); *C07K 2317/622* (2013.01); *C07K 2317/73* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,150,149 A | 4/1979 | Wolfsen et al. |
| 4,361,544 A | 11/1982 | Goldenberg |
| 4,444,744 A | 4/1984 | Goldenberg |
| 4,737,456 A | 4/1988 | Weng et al. |
| 5,202,238 A | 4/1993 | Fell, Jr. et al. |
| 5,204,244 A | 4/1993 | Fell et al. |
| 5,571,894 A | 11/1996 | Wels et al. |
| 5,587,458 A | 12/1996 | King et al. |
| 5,731,168 A | 3/1998 | Carter et al. |
| 5,747,654 A | 5/1998 | Pastan et al. |
| 5,789,199 A | 8/1998 | Joly et al. |
| 5,798,229 A | 8/1998 | Strittmatter et al. |
| 5,821,333 A | 10/1998 | Carter et al. |
| 5,840,523 A | 11/1998 | Simmons et al. |
| 5,869,046 A | 2/1999 | Presta et al. |
| 5,959,083 A | 9/1999 | Bosslet et al. |
| 5,959,177 A | 9/1999 | Hein et al. |
| 6,040,498 A | 3/2000 | Stomp et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 * | 5/2001 | Davis et al. ............ 530/387.3 |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,511,663 B1 | 1/2003 | King et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,658,672 B2 | 12/2003 | Hsieh |
| 6,737,056 B1 | 5/2004 | Presta |
| 6,897,044 B1 | 5/2005 | Braslawsky et al. |
| 6,946,292 B2 | 9/2005 | Kanda et al. |
| 6,982,321 B2 | 1/2006 | Winter |
| 7,125,978 B1 | 10/2006 | Vezina et al. |
| 7,129,330 B1 | 10/2006 | Little et al. |
| 7,355,008 B2 | 4/2008 | Stavenhagen et al. |
| 7,381,408 B2 | 6/2008 | Mezo et al. |
| 7,642,228 B2 | 1/2010 | Carter et al. |
| 7,651,688 B2 | 1/2010 | Hanai et al. |
| 7,666,622 B2 * | 2/2010 | Sharma et al. ............ 435/69.1 |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 8,216,805 B2 | 7/2012 | Carter et al. |
| 8,227,577 B2 | 7/2012 | Klein et al. |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Mallender et al (JBC, 271(10):5338-5346, 1996).*
Labrijn et al (JI, 187:3238-3246, 2011).*
Rose et al (Structure, 19:1274-1282, 2011).*
International Search Report dated Aug. 31, 2009, in the EP 09005108.7 application.
Merchant et al., Nature Biotechnology 16:677-681 ( 1998).
Shen et al., Journal of Immunological Methods 318:65-74 ( 2007).
Hust et al., BMC Biotechnology 7:14 ( 2007).
Gold et al., Cancer Res. (XP-002541923), 68(12):4819 ( 2008).
Ridgway, J.B.B. (1996). "Knobs-into-holes engineering of antibody $C_H3$ domains for heavy chain heterodimerixation," *Protein Engineering* 9(7):617-621.

(Continued)

*Primary Examiner* — Brad Duffy
(74) *Attorney, Agent, or Firm* — Morrison & Foerster LLP

(57) ABSTRACT

The present invention relates to trivalent, bispecific antibodies, methods for their production, pharmaceutical compositions containing the antibodies, and uses thereof.

11 Claims, 13 Drawing Sheets

(56) References Cited

U.S. PATENT DOCUMENTS

| | | |
|---|---|---|
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Junutula et al. |
| 8,796,424 B2 | 8/2014 | Croasdale et al. |
| 2002/0155537 A1 | 10/2002 | Carter et al. |
| 2003/0124129 A1 | 7/2003 | Oliner |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Mertens et al. |
| 2004/0259075 A1 | 12/2004 | Dimitrov et al. |
| 2005/0054048 A1 | 3/2005 | Grasso et al. |
| 2005/0064509 A1 | 3/2005 | Bradbury et al. |
| 2005/0079170 A1 | 4/2005 | Le Gall et al. |
| 2005/0123476 A1 | 6/2005 | Bugge et al. |
| 2005/0152894 A1 | 7/2005 | Krummen et al. |
| 2005/0163782 A1 | 7/2005 | Glaser et al. |
| 2005/0249722 A1 | 11/2005 | Beliard et al. |
| 2005/0260186 A1 | 11/2005 | Bookbinder et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Hoogenboom et al. |
| 2006/0280747 A1 | 12/2006 | Fuh et al. |
| 2007/0071675 A1* | 3/2007 | Wu et al. ............ 424/1.49 |
| 2007/0071742 A1 | 3/2007 | Fang et al. |
| 2007/0141065 A1 | 6/2007 | Fuh et al. |
| 2007/0269369 A1* | 11/2007 | Gegg et al. ............ 424/1.41 |
| 2007/0274985 A1 | 11/2007 | Dubel et al. |
| 2007/0274998 A1 | 11/2007 | Utku |
| 2008/0187954 A1 | 8/2008 | Kallmeier et al. |
| 2008/0234183 A1 | 9/2008 | Hallbrink et al. |
| 2009/0023811 A1 | 1/2009 | Biadatti et al. |
| 2009/0060910 A1* | 3/2009 | Johnson ........... C07K 16/283 424/133.1 |
| 2009/0155275 A1* | 6/2009 | Wu et al. ............ 424/136.1 |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 8/2009 | Kobaru |
| 2009/0232811 A1 | 9/2009 | Klein et al. |
| 2010/0081796 A1 | 4/2010 | Brinkmann et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256340 A1 | 10/2010 | Brinkmann et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0029481 A1 | 2/2012 | Pech et al. |
| 2012/0149879 A1 | 6/2012 | Brinkmann et al. |
| 2012/0164726 A1 | 6/2012 | Klein et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0249296 A1 | 9/2014 | Ploegh |
| 2014/0294810 A1 | 10/2014 | Lowman et al. |
| 2014/0370019 A1 | 12/2014 | Bruenker et al. |
| 2015/0166670 A1 | 6/2015 | Castoldi et al. |
| 2015/0232541 A1 | 8/2015 | Fenn |
| 2015/0232560 A1 | 8/2015 | Heindl et al. |
| 2015/0291704 A1 | 10/2015 | Beck |

FOREIGN PATENT DOCUMENTS

| | | |
|---|---|---|
| CN | 12320239 A | 10/1999 |
| CN | 1603345 | 4/2005 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 B1 | 3/1989 |
| EP | 0 307 434 B2 | 3/1989 |
| EP | 0 637 593 A1 | 2/1995 |
| EP | 1 870 459 A1 | 12/2007 |
| EP | 2 050 764 A1 | 4/2009 |
| EP | 2 443 154 B1 | 4/2012 |
| JP | 2008-531049 A | 8/2008 |
| RU | 2005/1242810 A | 1/2006 |
| RU | 2295537 C2 | 3/2007 |
| WO | WO-93/01161 A1 | 1/1993 |
| WO | WO-93/06217 A1 | 4/1993 |
| WO | WO-93/16185 A2 | 8/1993 |
| WO | WO-93/16185 A3 | 8/1993 |
| WO | 94/09131 | 4/1994 |
| WO | WO-94/09131 A1 | 4/1994 |
| WO | WO-94/10202 A1 | 5/1994 |
| WO | WO-94/29350 A2 | 12/1994 |
| WO | WO-94/29350 A3 | 12/1994 |
| WO | WO-95/09917 A1 | 4/1995 |
| WO | WO-96/27011 A1 | 9/1996 |
| WO | WO-96/27612 A1 | 9/1996 |
| WO | WO-97/01580 A1 | 1/1997 |
| WO | WO-97/14719 A1 | 4/1997 |
| WO | WO-97/28267 A1 | 8/1997 |
| WO | WO-97/28267 C1 | 8/1997 |
| WO | WO-98/45331 A2 | 10/1998 |
| WO | WO-98/45331 A3 | 10/1998 |
| WO | WO-98/45332 A2 | 10/1998 |
| WO | WO-98/45332 A3 | 10/1998 |
| WO | WO-98/48032 A2 | 10/1998 |
| WO | WO-98/48032 A3 | 10/1998 |
| WO | WO-99/37791 A1 | 7/1999 |
| WO | WO-99/51642 A1 | 10/1999 |
| WO | WO-99/54342 A1 | 10/1999 |
| WO | 99/66951 | 12/1999 |
| WO | WO-00/35956 A1 | 6/2000 |
| WO | WO-00/61739 A1 | 10/2000 |
| WO | WO-01/77342 A1 | 10/2001 |
| WO | WO-01/085795 A1 | 11/2001 |
| WO | WO-01/90192 A2 | 11/2001 |
| WO | WO-02/02781 A1 | 1/2002 |
| WO | WO-02/096948 A2 | 12/2002 |
| WO | WO-03/030833 A2 | 4/2003 |
| WO | WO-03/030833 A3 | 4/2003 |
| WO | WO-03/035835 A2 | 5/2003 |
| WO | WO-03/035835 A3 | 5/2003 |
| WO | WO-03/055993 A1 | 7/2003 |
| WO | WO-03/057134 A2 | 7/2003 |
| WO | WO-03/057134 A3 | 7/2003 |
| WO | WO-03/073238 A2 | 9/2003 |
| WO | WO-03/073238 A3 | 9/2003 |
| WO | WO-03/097105 A1 | 11/2003 |
| WO | WO-03/106501 A1 | 12/2003 |
| WO | 2004/032961 | 4/2004 |
| WO | WO-2004/058298 A1 | 7/2004 |
| WO | 2004/072117 | 8/2004 |
| WO | WO-2004/065540 A2 | 8/2004 |
| WO | WO-2004/065540 A3 | 8/2004 |
| WO | WO-2005/000900 A1 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO 2005001025 A2 * | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035727 A2 | 4/2005 |
| WO | WO-2005/035727 A3 | 4/2005 |

(56) References Cited

FOREIGN PATENT DOCUMENTS

| WO | WO-2005/044853 A2 | 5/2005 |
|---|---|---|
| WO | WO-2005/044853 A3 | 5/2005 |
| WO | WO-2005/044859 A2 | 5/2005 |
| WO | WO-2005/044859 A3 | 5/2005 |
| WO | WO-2005/051976 A2 | 6/2005 |
| WO | WO-2005/063816 A2 | 7/2005 |
| WO | WO-2005/063816 A3 | 7/2005 |
| WO | WO-2005/074524 A2 | 8/2005 |
| WO | WO-2006/020258 A2 | 2/2006 |
| WO | WO-2006/020258 A3 | 2/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | 2006/091209 | 8/2006 |
| WO | WO-2006/082515 A2 | 8/2006 |
| WO | WO-2006/082515 A3 | 8/2006 |
| WO | WO-2006/093794 A1 | 9/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2007/024715 A2 | 3/2007 |
| WO | WO-2007/031875 A2 | 3/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/085837 A1 | 8/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/108013 A2 | 9/2007 |
| WO | WO-2007/108013 A3 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/14901 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/077077 A2 | 6/2008 |
| WO | WO-2008/077077 A3 | 6/2008 |
| WO | WO-2008/077546 A1 | 7/2008 |
| WO | 2008/100624 | 8/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/032782 A2 | 3/2009 |
| WO | WO-2009/032782 A3 | 3/2009 |
| WO | 2009/018386 | 5/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2009/126944 A1 | 10/2009 |
| WO | WO-2010/034441 A1 | 4/2010 |
| WO | WO-2010/035012 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO-2010/087994 A2 | 8/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/115598 A1 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/025525 A1 | 3/2012 |
| WO | WO-2012/025530 A1 | 3/2012 |
| WO | WO-2012/058768 A1 | 5/2012 |
| WO | WO-2012/116927 A1 | 9/2012 |
| WO | WO-2013/003555 A1 | 1/2013 |
| WO | WO-2013/026833 A1 | 2/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/012085 A2 | 1/2014 |
| WO | WO-2014/049003 A1 | 4/2014 |
| WO | WO-2014/144357 A1 | 9/2014 |
| WO | WO-2016/055432 A2 | 4/2016 |
| WO | WO-2016/055432 A3 | 4/2016 |
| WO | WO-2016/087416 A1 | 6/2016 |

OTHER PUBLICATIONS

Aggarwal et al., (Jan. 22, 2008). "Fibroblast Activation Proten Peptide Substrates Identified from Human Collagen I Derived Gelatin Cleavage Sites," *Biochemistry* 47(3):1076-1086, (Jan. 22, 2008).

Anonymous., "Production in yeasts of stable antibody fragments," *Expert Opinion on Therapeutic Patents* 7(2):179-183, (1997).

Atwell et al., "Stable heterodimers from remodeling the domain interface of a homodimer using a phage display library" *J. Mol. Biol.* 270 (1):26-35 (1997).

Ausubel et al., Current Protocols in Molecular Biology, Greene Publishing and Wiley Interscience, New York, New York, (Table of Contents), (1987).

Avgeris et al., "Kallikrein-related peptidase genes as promising biomarkers for prognosis and monitoring of human malignancies," *Biol. Chem* 391(5):505-511, (May 2010).

Bao et al., "HER2-mediated upregulation of MMP-1 is involved in gastric cancer cell invasion," *Arch Biochem Biophys* 499(1-2):49-55, (Jul. 2010).

Barnes et al., "Advances in animal cell recombinant protein production: GS-NS0 expression system" *Cytotechnology* 32 (2):109-23 (Feb. 2000).

Barnes et al., "Characterization of the stability of recombinant protein production in the GS-NS0 expression system" *Biotechnol Bioeng.* 73(4):261-70 (May 2001).

Bera et al., "A bivalent disulfide-stabilized Fv with improved antigen binding to erbB2," *J. Mol. Biol.* 281(3):475-483, (Aug. 21, 1998).

Boado et al., "IgG-single chain Fv fusion protein therapeutic for Alzheimer's disease: Expression in CHO cells and pharmacokinetics and brain delivery in the rhesus monkey," *Biotechnology and Bioengineering* 105(3):627-635, (Feb. 15, 2010).

(56) References Cited

OTHER PUBLICATIONS

Boerner et al., "Production of Antigen—Specific Human Monoclonal Antibodies From In Vitro-Primed Human Splenocytes" *J. Immunol.* 147(1):86-95, (Jul. 1991).
Borgstrom et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Briggs et al., "Cystatin E/M suppresses legumain activity and invasion of human melanoma," *BMC Cancer* 10(17):1-13, (Jan. 2010).
Brinkmann et al., "Disulfide-stabilized Fv fragments," Chapter 14 in Antibody Engineering, Kontermaan et al. eds., vol. 2, Springer-Verlag, Berlin Heidelberg, Germany, pp. 181-189, (Apr. 30, 2010).
Brüggemann et al., "Comparison of the effector functions of human immunoglobulins using a matched set of chimeric antibodies" *J Exp Med.* 166(5):1351-61, (Nov. 1987).
Brüggemann et al., "Designer Mice: The Production of Human Antibody Repertoires in Transgenic Animals" *Year in Immuno.* 7:33-40, (1993).
Brunhouse et al., "Isotypes of IgG: comparison of the primary structures of three pairs of isotypes which differ in their ability to activate complement" Mol Immunol. 16(11): 907-917 (Nov. 1979).
Burgess et al., "Possible dissociation of the heparin-binding and mitogenic activities of heparin-binding (acidic fibroblast) growth factor-1 from its receptor-binding activities by site-directed mutagenesis of a single lysine residue," *Journal of Cell Biology* 111:2129-2138, (Nov. 1990).
Burton et al., "The C1q Receptor Site on Immunoglobulin G." *Nature* 288(5789):338-344, (Nov. 27,1980).
Caron et al., "Engineered humanized dimeric forms of IgG are more effective antibodies," *J. Exp. Med.* 176(4):1191-1195, (Oct. 1, 1992).
Carro et al., "Serum insulin-like growth factor I regulates brain amyloid-β levels," *Nature Medicine* 8(12):1390-1397, (2002, e-pub. Nov. 4, 2002).
Carter et al., "Humanization of an Anti-PI85$^{HER2}$ Antibody for Human Cancer Therapy" *Proc Natl Acad Sci USA*. 89(10): 4285-4289 (May 1992).
Carter., "Bispecific human IgG by design," *Immunol. Methods* 248:7-15. (2001).
Chan et al., "Variable Region Domain Exchange in Human IgGs Promotes Antibody Complex Formation with Accompanying Structural Changes and Altered Effector Functions," *Molecular Immunology* 41:(5)527-538, (2004).
Chitnis et al., "The type 1 insulin-like growth factor receptor pathway," *Clin. Cancer Res.* 14(20):6364-6370, (Oct. 15, 2008).
Chung et al., "Development of a novel albumin-binding prodrug that is cleaved by urokinase-type-plasminogen activator (uPA)," *Bioorg Med Chem Lett*. 16(19):5157-5163 (Oct. 1, 2006).
Cohen et al., "Nonchromosomal antibiotic resistance in bacteria: Genetic transformation of *Escherichia coli* by R-factor DNA," *Proc. Natl. Acad. Sci. USA* 69(8):2110-2114 (Aug. 1972).
Cole et al., "The EBV-hybridoma technique and its application to human lung cancer" *Monoclonal Antibodies and Cancer Therapy*, New York: Alan R. Liss, Inc. pp. 77-96 (1985).
Coloma and Morrison., "Design and production of novel tetravalent bispecific antibodies" *Nature Biotechnology* 15(2):159-163 (Feb. 1997).
Cordingley et al., "Substrate requirements of human rhinovirus 3C protease for peptide cleavage in vitro," *J. Biol. Chem.* 265(16):9062-9065, (1990).
Cortesio et al., "Calpain 2 and PTP1B function in a novel pathway with Src to regulate invadopodia dynamics and breast cancer cell invasion," *J. Cell Biol.* 180(5):957-971, (Mar. 10, 2008).
Coxon et al., "Combined treatment of angiopoietin and VEGF pathway antagonists enhances antitumor activity in preclinical models of colon carcinoma," *99th AACR Annual Meeting*, Abstract #1113, (Apr. 2008).
Crawford et al., "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).
Cudic et al. "Extracellular proteases as targets for drug development," *Curr. Protein Pept Sci* 10(4):297-307, (Aug. 2009).
Cullen et al., "Granzymes in cancer and immunity," *Cell Death Differ* 17(4):616-623, (Apr. 2010).
Davies et al., "Expression of GnTIII in a recombinant antI•CD20 CHO production cell line: Expression of antibodies with altered glycoforms leads to an increase in ADCC through higher affinity for FcγRIII," *Biotechnol. Bioeng.* 74:288-294, (2001).
Deyev., "Multivalency: the hallmark of antibodies used for optimization of tumor targeting by design," *Bioessays* 30(9):904-918, (2008).
Donaldson et al., "Design and development of masked therapeutic antibodies to limit off-target effects: Application to anti-EGFR antibodies," *Cancer Biology & Therapy* 8(22):2145-2150, (Nov. 15, 2009).
Durocher et al., "High-level and high-throughput recombinant protein production by transient transfection of suspension-growing human 293-EBNA1 cells," Nucleic Acids Research•30(2 e9):nine pages, (2002).
Edelman et al., "The covalent structure of an entire γG immunoglobulin molecule" Proc. Natl. Acad. Sci. USA 63:78-85, (1969).
Fischer et al., "Bispecific antibodies: Molecules that enable novel therapeutic strategies" *Pathobiology* 74:3-14, (2007).
Flatman et al., "Process analytics for purification of monoclonal antibodies," *J. Chromatogr B* 848:79-87, (2007).
Galamb et al., "Inflammation, adenoma and cancer: objective classification of colon biopsy specimens with gene expression signature," *Dis Markers* 25(1):1-16, (2008).
Geisse et al., "Eukaryotic expression systems: A comparison" *Protein Expression and Purification* 8:271-282 (1996).
Gerspach et al., "Target-selective activation of a TNF prodrug by urokinase-type plasminogen activator (uPA) mediated proteolytic processing at the cell surface," *Cancer Immunol. Immunother* 55:1590-1600 (2006).
Goldenberg et al., "Bi-Specific Antibodies that Bind Specific Target Tissue and Targeted Conjugates," Derwent Information Ltd., 12 pages, (2012).
Graham et al., "A new technique for the assay of infectivity of human adenovirus 5 DNA" *Virology* 52 (2):456-467, (1973).
Grote et al., "Bispecific Antibody Derivatives Based on Full-Length IgG Formats," Chapter 16 in *Methods in Molecular Biology* 901:247-263, (2012).
Hartog et al., "The Insulin-like growth factor 1 receptor in cancer: Old focus, new future," European Journal of Cancer, Pergamon Press, Oxford, GB, 43(13):1895-1904, (Aug. 23, 2007).
Henry et al., "Clinical implications of fibroblast activation protein in patients with colon cancer," *Clin Cancer Res.* 13(6):1736-1741, (Mar. 15, 2007).
Hezareh et al., "Effector Function Activities of a Panel of Mutants of a Broadly Neutralizing Antibody against Human Immunodeficiency Virus Type 1" *Journal of Virology* 75(24):12161-12168, (Dec. 2001).
Hollander., "Bispecific antibodies for cancer therapy," *Immunotherapy* 1(2):211-222, (Mar. 2009).
Holliger et al., "Engineered antibody fragments and the rise of single domains" *Nat Biotechnol.* 23(9):1126-1136, (Sep. 2005).
Hoogenboom and Winter., "By-passing immunisation. Human antibodies from synthetic repertoires of germline VH gene segments rearranged in vitro" *J Mol Biol.* 227 (2):381-388, (Sep. 20, 1992).
Ibragimova et al., "Stability of the β-Sheet of the WW domain: A molecular dynamics simulation study," *Biophysical Journal* 77:2191-2198, (Oct. 1999).
Idusogie et al., "Mapping of the C1q binding site on rituxan, a Chimeric antibody with a human IgG1 Fc" The Journal of Immunology 164:4178-4184, (2000).
International Search Report dated Dec. 6, 2011, for PCT Patent Application No. PCT/EP2011/064476 filed on Aug. 23, 2011, seven pages.

(56) References Cited

OTHER PUBLICATIONS

International Search Report dated Dec. 6, 2011, for PCT Patent Application No. PCT/EP2011/064468 filed on Aug. 23, 2011, seven pages.
Jakobovits et al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90(6) :2551-2555, (Mar. 15, 1993).
Jakobovits et al., "Germ-line Transmission and Expression of a Human-derived Yeast Artificial Chromosome" *Nature* 362:255-258, (Mar. 1993).
Jefferis et al., "IgG-Fc-mediated effector functions: molecular definition of interaction sites for effector ligands and the role of glycosylation" *Immunol Rev.* 163:59-76, (1998).
Jendreyko et al., Simultaneous, Phenotypic Knockout of VEGF-R2 and Tie-2 With an Intradiabody Enhances Antiangiogenic Effects In Vivo; Therapieoptimierung und Risikostratifizierung, Scripps Research Institute, 218:143-151, (2006).
Jia et al. "A novel trifunctional IgG-like bispecific antibody to inhibit HIV-1 infection and enhance lysis of HIV by targeting activation of complement," *Virology Journal* 7(142):1-4, (Jun. 29, 2010).
Johnson et al., "Kabat Database and its applications: 30 years after the first variability plot" *Nucleic Acids Research* 28(1) :214-218, (2000).
Kabat et al., "Evolutionary and structural influences on light chain constant (C) region of human and mouse immunoglobulins" *Proc. Natl. Acad. Sci. USA* 72(7) :2785-2788, (Jul. 1975).
Kabat et al., Sequences of Proteins of Immunological Interest (Table of Contents and Introduction), 5th edition, Bethesda, MD: Public Health Service, NIH, vol. 1, (1991).
Karadag et al., "ADAM-9 (MDC-9/meltrin-γ), a member of the a disintegrin and metalloproteinase family, regulates myeloma-cell-induced interleukin-6 production in osteoblasts by direct interaction with the alpha(v)beta5 integrin," *Blood* 107(8):3271-3278, (Apr. 2006).
Kaufman., "Overview of Vector Design for Mammalian Gene Expression" *Molecular Biotechnology* 16:151-160, (2000).
Kazama et al., "Hepsin, a putative membrane-associated serine protease, activates human factor VII and initiates a pathway of blood coagulation on the cell surface leading to thrombin formation," *JBC* 270:66-72, (1995).
Kim et al., Inhibition of Vascular Endothelial Growth Factor-Induced Angiogenesis Suppresses Tumour Growth In Vivo, *Nature* 362:841-844, (1993).
Kleinschmidt et al., "Design of a modular immunotoxin connected by polyionic adapter peptides," *J. Mol. Biol.* 327(2):445-452, (Mar. 21, 2003).
Kobayashi et al., "Similarities in the Biodistribution of Iodine-Labeled Anti•Tac Single-Chain Disulfide-Stabilized Fv Fragment and Anti-Tac Disulfide-Stabilized Fv Fragment," *Nuclear Medicine & Biology* 25:387-393, (1998).
Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Lamkanfi et al., "Inflammasomes: guardians of cytosolic sanctity," *Immunol. Rev.* 227(1):95-105, (Jan. 2009).
Lazar et al., "Transforming growth factor α: Mutation of aspartic acid 47 and leucine 48 results in different biological activities," *Molecular and Cellular Biology* 8(3):1247-1252, (Mar. 1988).
Lee et al., "Using substrate specificity of antiplasmin-cleaving enzyme for fibroblast activation protein inhibitor design," *Biochemistry* 48(23):5149-5158, (Jun. 16, 2009).
Leeman et al., "The Structure, Regulation, and Function of Human Matrix Metalloproteinase-13," *Crit. Rev Biochem Mol. Biol.* 37(3):149-166, (2002).

Lifely et al., "Glycosylation and Biological Activity of CAMPATH-1H Expressed in Different Cell Lines and Grown Under Different Culture Conditions." *Glycobiology* 5(8):813-822, (Dec. 1995).
Lin et al., "Structure-Function relationships in glucagon: Properties of highly purified des-his-, monoiodo-, and [Des-Asn[28], Thr[29]](homoserine lactone[27])-glucagon," *Biochemistry USA* 14:1559-1563, (1975).
Liang et al., Cross-species Vascular Endothelial Growth Factor (VEGF)-blocking Antibodies Completely Inhibit the Growth of Human Tumor Xenografts and Measure the Contribution of Stromal VEGF; Journal of Biological Chemistry, 281(2):951-961, (2006).
Liotta et al., "Metastatic potential correlates with enzymatic degradation of basement membrane collagen," *Nature* 284(5751) 67-68, (Mar. 6, 1980).
Liu et al., "Clinical and imaging diagnosis of primary hepatic lymphoma," *J First Mil Med. Univ*, 25(10):1290-1292, three pages, (2005). (Translation of the Abstract Only.).
Lopez-Otin et al., "The regulatory crosstalk between kinases and proteases in cancer," *Nat. Rev. Cancer* 10(4):278-292, (Apr. 2010).
Love et al., "Recombinant antibodies possessing novel effector functions" *Methods in Enzymology* 178:515-527, (1989).
Lu et al., "A Fully Human Recombinant IgG-Like Bispecific Antibody to Both the Epidermal growth Factor Receptor and the Insulin-Like Growth Factor Receptor for Enhanced Antitumor Activity," The Journal of Biological Chemistry 280(20):19665-19672, (May 20, 2005).
Lu et al., "ADAMTS1 and MMP1 proteolytically engage EGF-like ligands in an osteolytic signaling cascade for bone metastasis," Genes Dev. 23(16):1882-1894, (Aug. 2009).
Lukas et al., "Inhibition of C1-Mediated Immune Hemolysis by Monomeric and Dimeric Peptides from the Second Constant Domain of Human Immunoglobulin G1" *The Journal of Immunolgy* 127(6):2555-2560, (Dec. 1981).
Lund et al., "Oligosaccharide-protein interactions in IgG can modulate recognition by Fcγ receptors" *FASEB Journal* 9:115-119, (1995).
Makrides., "Components of Vectors for Gene Transfer and Expression in Mammalian Cells" *Protein Expression and Purification* 17:183-202, (1999).
Mamoune et al., "Calpain-2 as a target for limiting prostate cancer invasion," *Cancer Res.* 63(15):4632-4640, (Aug. 2003).
Marks et al., "By-Passing Immunization: Human Antibodies From V-gene Libraries Displayed on Phage" *J Mol Biol.* 222(3) :581-597, (Dec. 5, 1991).
Marvin et al. "Recombinant approaches to IgG-like bispecific antibodies," *Acta Pharmacol. Sin.* 26:649-658, (2005).
Marvin et al., "Bispecific antibodies for dual-modality cancer therapy: killing two signaling cascades with one stone," *Curr. Opin. Drug Discov. Devl.* 9:184-193, (2006).
Matrisian. "Cancer biology: extracellular proteinases in malignancy," *Curr. Biol.* 9(20):R776-R778, (Oct. 1999).
Meissner et al., "Transient Gene Expression: Recombinant Protein Production with Suspension-Adapted HEK293-EBNA Cells" *Biotechnology and Bioengineering* 75:197-203, (2001).
Melnyk et al., Vascular Endothelial Growth Factor Promotes Tumor Dissemination by a Mechanism Distinct from Its Effect on Primary Tumor Growth, *Cancer Research* 56:921-924, (1996).
Merchant et al., "An efficient route to human bispecific IgG" *Nature Biotechnology* 16:677-681, (1998).
Michaelson et al., "Anti-tumor activity of stability-engineered IgG-like bispecific antibodies targeting TRAIL-R2 and LTβR," *MAbs* 1(2):128-141, (Mar. 2009, e-pub. Mar. 11, 2009).
Miller et al., "Design, Construction, and In Vitro Analyses of Multivalent Antibodies," *J. Immunol.* 170:4854-4861, (2003).
Milstein et al., "Hybrid Hybridomas and Their Use in Immunohistochemistry" *Nature* 305: 537-540, (Oct. 6, 1983).
Mimura et al., "Role of Oligosaccharide Residues of IgG1-Fc in FcγRIIb Binding" *The Journal of Biological Chemistry* 276(49): 45539-45547, (Dec. 7, 2001).
Minn et al., "Genes that Mediate Breast Cancer Metastasis to Lung," *Nature* 436(7050):518-524, (Jul. 2005).

(56) References Cited

OTHER PUBLICATIONS

Morgan et al., "The N-terminal End of the CH2 Domain of Chimeric Human IgG1 anti-HLA-DR is Necessary for C1q, FcγRIII Binding" *Immunology* 86:319-324, (1995).
Morrison et al., "Chimeric Human Antibody Molecules: Mouse Antigen-Binding Domains with Human Constant Region Domains" *Proc. Natl. Acad. Sci. USA* 81(21):6851-6855, (Nov. 1984).
Morrison et al., "Variable region domain exchange influences the functional properties of IgG" *Journal of Immunology, American Association of Immunologiest* 160:2802-2808, (Jan. 1, 1998).
Morrison. "Two Heads are Better than One," *Nature Biotechnology* 25(11):1233-1234, (Nov. 2007).
Morrison. "Success in Specification" *Nature* 368:812-813, (Apr. 1994).
Müller et al., "The first constant domain ($C_H1$ and $C_L$) of an antibody used as heterodimerization domain for bispecific miniantibodies," *FEBS Letters* 422:259-264, (1998).
Müller et al., "Recombinant Bispecific Antibodies for Cellular Cancer Immunotherapy," *Current Opinion in Molecular Therapeutics* 9:319-326, (2007).
Müller et al., "Bispecific Antibodies," Chapter 2 in Handbook of Therapeutic Antibodies, Dübel, S. ed., Wiley-VCH Verlag GmbH & Company KGaA, Weinheim, pp. 345-378, (2007).
Mukhopadhyay et al., "Matrix metalloproteinase-12 is a therapeutic target for asthma in children and young adults," *J. Allergy Clin Immunol.* 126:70-76, (2010).
Netzel-Arnett et al., "Sequence Specificities of Human Fibroblast and Neutrophil Collagenases," *J. Biol. Chem.* 266(11):6747-6755, (Apr. 15, 1991).
Netzel-Arnett et al., "Comparative sequence specificities of human 72- and 92-kDa gelatinases (type IV collagenases) and PUMP (matrilysin)," *Biochemistry* 32(25):6427-6432, (Jun. 29, 1993).
Neuberger et al., "A hapten-specific chimaeric IgE antibody with human physiological effector function," *Nature* 314:268-270, (Mar. 21, 1985).
Niwa et al. "IgG subclass-independent improvement of antibody-dependent cellular cytotoxicity by fucose removal from $Asn^{297}$-linked oligosaccharides," *J. Immunol. Methods* 306:151-160, (2005).
Norderhaug et al., "Versatile Vectors for Transient and Stable Expression of Recombinant Antibody Molecules in Mammalian Cells," *Journal of Immunological Methods* 204:77-87, (1997).
Ohno et al., "Antigen-binding specificities of antibodies are primarily determined by seven residues of $V_H$," *Proc. Natl. Acad. Sci. USA* 82(9):2945-2949, (May 1985).
Oliner et al., Suppression of Angiogenesis and Tumor Growth by Selective Inhibition of Angiopoietin-2, *Cancer Cel* 6:507-516, (2004).
Orcutt, et al. "A modular IgG-scFv bispecific antibody topology," *Protein Engineering, Design & Selection* 23(4):221-228, (Apr. 2010, e-pub. Dec. 17, 2009).
Orlandi et al., "Cloning Immunoglobulin Variable Domains for Expression by the Polymerase Chain Reaction" *Proc. Natl. Acad. Sci. USA* 86:3833-3837, (May 1989).
Pace et al., "How to Measure and Predict the Molar Absorption Coefficient of a Protein" *Protein Science* 4(11): 2411-2423, (Nov. 1995).
Pakula et al., "Genetic analysis of protein stability and function," *Annu. Rev. Genet.* 23:289-310, (1989).
Plückthun et al., "New Protein Engineering Approaches to Multivalent and Bispecific Antibody Fragments," *Immunotechnology* 3:83-105, (1997).
PreScission Protease, GE Healthcare Catalogue No. 27-0843-01, located at http://www.gelifesciences.com/webapp/wcs/stores/servlet/productByld/en/GELifeScience, last visited on Jul. 10, 2013, one page.
Radaev et al., "Recognition of IgG by Fcγ Receptor," *The Journal of Biological Chemistry* 276(19): 16478-16483, (May 11, 2001).
Rajgopal et al., "A Form of Anti-Tac(Fv) Which is Both Single-chain and Disulfide Stabilized: Comparison with its single chain and Disulfide-stabilized Homologs," *Protein Engineering* 10(12):1453-1459, (1997).
Raju., "Glycosylation Variations with Expression Systems and Their Impact on Biological Activity of Therapeutic Immunoglobulins," *BioProcess International* 1(4): 44-53, (Apr. 2003).
Rawlings., "A large and accurate collection of peptidase cleavages in the MEROPS database," Database (Oxford), pp. 1-14, (2009, e-pub. Nov. 2, 2009).
Reiter et al., "Improved binding and antitumor activity of a recombinant anti-erbB2 immunotoxin by disulfide stabilization of the Fv fragment," *JBC* 269:18327-18331, (1994).
Reiter et al., "Cytotoxic and antitumor activity of a recombinant immunotoxin composed of disulfide-stabilized anti-Tac Fv fragment and truncated Pseudomonas exotoxin," *International Journal of Cancer* 58:142-149, (1994).
Reiter et al., "Antitumor activity and pharmacokinetics in mice of a recombinant immunotoxin containing a disulfide-stabilized Fv fragment," *Cancer Research* 54:2714-2718, (1994).
Reiter et al., "Antibody engineering of recombinant Fv immunotoxins for improved targeting of cancer: disulfide-stabilized Fv immunotoxins," *Clin. Cancer Res.* 2(2):245-252, (Feb. 1, 1996).
Reiter et al., "Construction of a functional disulfide-stabilized TCR Fv indicates that antibody and TCR Fv frameworks are very similar in structure," *Immunity* 2:281-287, (1995).
Riechmann et al., "Reshaping Human Antibodies for Therapy" *Nature* 332:323-327, (Mar. 24,1988).
Roitt et al., "Immunology" English Translation by McElroy Translation Company, Moscow "Mir" (2000), p. 110-111, eight pages.
Rossi, E.A. et al., "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).
Routier et al., "The Glycosylation Pattern of a Humanized IgGI Antibody (D1.3) Expressed in CHO Cells" *Glycoconjugate Journal* 14:201-207, (1997).
Ruppert et al., "Protease levels in breast, ovary and other gynecological tumor tissues: prognostic importance in breast cancer," *Cancer Detect. Prev.* 21(5):452-459, (1997).
Sambrook et al., Molecular Cloning: A Laboratory Manual "The Table of Contents" Cold Spring Harbor, New York: Cold Spring Harbor Laboratory Press, (1989).
Schaefer et al., "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schlaeger., "The Protein Hydrolysate, Primatone RL, is a Cost Effective Multiple Growth Promoter of Mammalian Cell Culture in Serum-containing and Serum-free Media and Displays Anti apoptosis Properties," *Journal of Immunological Methods* 194:191-199, (1996).
Schlaeger et al., "Transient Gene Expression in Mammalian Cells Grown in Serum-free Suspension Culture," *Cytotechnology* 30:71-83, (1999).
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al., "Expression of a bispecific dsFv-dsFv' antibody fragment in *Escherichia coli*," *Protein Engineering* 13(10):725-734, (Oct. 2000).
Schoonjans, et al., Fab Chains As an Efficient Heterodimerazation Scaffold for the Production of Recombinant Bispecific and Trispecific Antibody Derivatives, *Journal of Immunology* 165:7050-7057, (2000).
Schwartz et al., "A superactive insulin: [B10-aspartic acid]insulin(human)," *Proc. Natl. Acad. Sci. USA* 84:6408-6411, (Sep. 1987).
Scott et al., "Biologic protease inhibitors as novel therapeutic agents," *Biochimie* 92(11):1681-1688, (Nov. 2010).

(56) References Cited

OTHER PUBLICATIONS

Shen et al. "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Shields et al., "High Resolution Mapping of the Binding Site on Human IgG1 for FvγRI, FcγRII, FcγRIII and FcRn and Design of IgG1 Variants with Improved Binding to the FcγR," *Journal of Biological Chemistry* 276 (9) :6591-6604, (2001).
Shields et al., "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al., "The Absence of Fucose but Not the Presence of galactose or Bisecting N-Acetylglucosamine of Huamn IgG1 Complex-Type Oligosaccharides Shows the Critical Role of Enhancing Antibodiy-Dependent Cellular cytotoxicity," *J. Biol. Chem.* 278 (5) 3466-3473, (2003).
Simmons et al., "Expression of full-length immunoglobulins in *Escherichia coli*: Rapid and Efficient production of aglycosylated antibodies" *Journal of Immunological Methods* 263:133-147, (2002).
Simon et al., "Antibody Domain Mutants Demonstrate Autonomy of the Antigen Binding Site" *The EMBO Journal* 9(4):1051-1056, (1990).
Stetler-Stevenson et al., "Progelatinase A activation during tumor cell invasion," *Invasion Metastasis* 14(1-6):259-268, (1994-1995).
Stevenson. "A chimeric antibody with dual Fc regions (bisFabFc) prepared by manipulations at the IgG hinge," *Anticancer Drug Des.* 3(4):219-230, (Mar. 1989).
Thommesen et al., "Lysine 322 in the human IgG3 $C_H2$ domain is crucial for antibody dependent complement activation," *Molecular Immunology* 37:995-1004, (2000).
Tripathi et al., "Laminin-332 is a substrate for hepsin, a protease associated with prostate cancer progression," *JBC* 283:30576-30584, (2008).
Umaña et al., "Engineered Glycoforms of an Antineuroblastoma IgG1 with Optimized Antibody-Dependent Cellular Cytotoxic Activity" *Nature Biotechnology* 17(2):176-180 (Feb. 1999).
U.S. Appl. No. 13/773,167, filed Feb. 21, 2013, for Brinkmann et al.
U.S. Appl. No. 13/773,013, filed Feb. 21, 2013, for Brinkmann et al.
Van Dijk and Van De Winkel., "Human antibodies as next generation therapeutics," *Curr Opin Chem Biol.* 5(4): 368-74, (Aug. 2001).
Van Spriel et al., "Immunotherapeutic perspective for bispecific antibodies," *Immunology Today* 21(8):391-397, (Aug. 2000).
Van'T Veer et al., "Gene expression profiling predicts clinical outcome of breast cancer," *Nature* 415(6871):530-536, (Jan. 2002).
Vazquez-Ortiz et al., "Overexpression of cathepsin F, matrix metalloproteinases 11 and 12 in cervical cancer," *BMC Cancer* 5:68, (Jun. 30, 2005).
Velasco et al., Human cathepsin O. Molecular cloning from a breast carcinoma, production of the active enzyme in *Escherichia coli*, and expression analysis in human tissues, *J. Biol Chem* 269(43):27136-27142, (Oct. 28, 1994).
Veveris-Lowe et al. Seminal Fluid Characterization for Male Fertility and Prostate Cancer: Kallikrein-Related Serine Proteases and whole Proteome Approaches, *Semin Thromb Hemost.* 33(1):87-99, (2007).
Vijayalakshmi., "Antibody Purification Methods" *Applied Biochemistry and Biotechnology* 75:93-102, (1998).
Walker et al., "Efficient and Rapid Affinity Purification of Proteins Using Recombinant Fusion Proteases," *Bio/Technology* 12:601-605, (1994).
Warren et al., Regulation of Vascular Endothelial Growth Factor of Human Colon Cancer Tumorigenesis in a Mouse Model of Experimental Liver Metastasis, *J. Clin. Invest.* 95:1789-1797, (1995).
Webber et al., "Preparation and characterization of a disulfide-stabilized Fv fragment of the anti-Tac antibody: comparison with its single-chain analog," *Molecular Immunology* 32:249-258, (1995).

Werner et al., "Appropriate Mammalian Expression Systems for Biopharmaceuticals" *Drug Research* 48(8):870-880, (1998).
Wielockx et al., "Matrilysin (matrix metalloproteinase-7): a new promising drug target in cancer and inflammation?," *Cytokine Growth Factor Rev.* 15(2-3):111-115, (Apr.-Jun. 2004).
Willems et al., "Optimizing expression and purification from cell culture medium of trispecific recombinant antibody derivatives" *Journal of Chromatography* B 786:161-176, (2003).
Woof et al., "Human antibody-FC receptor interactions illuminated by crystal structures," *Nat. Rev. Immunol.* 4:1-11, (2004).
Wright and Morrison, "Effect of Glycosylation on Antibody Function: Implications for Genetic Engineering," *Trends in Biotechnology* 15:26-32, (1997).
Wright et al., "ADAM28: a potential oncogene involved in asbestos-related lung adenocarcinomas," *Genes Chromosomes Cancer* 49(8);688-698, (Aug. 2010).
Written Opinion of the International Searching Authority dated Dec. 6, 2011, for PCT Patent Application No. PCT/EP2011/064476 filed on Aug. 23, 2011, four pages.
Written Opinion of the International Searching Authority dated Dec. 6, 2011, for PCT Patent Application No. PCT/EP2011/064468 filed on Aug. 23, 2011, four pages.
Wu et al., "Simultaneous Targeting of Multiple Disease Mediators by a Dual Variable-Domain Immunoglobulin" *Nature Biotechnology* 25(11):1290-1297, (Nov. 2007).
Xie et al., "A New format of bispecific antibody: Highly efficient heterodimerization, expression and tumor cell lysis," *J. of Immunol. Methods* 296:95-101, (2005).
Zeidler et al., "Simultaneous activation of T cells and accessory cells by a new class of intact bispecific antibody results in efficient tumor cell killing," *Journal of Immunology* 163:1246-1252, (1999).
Zuo et al. "An efficient route to the production of an IgG-like bispecific antibody," *Protein Engineering* 13(5):361-367, (2000).
Chilean Office Action dated Jan. 11, 2012, for Chilean Application No. 3781-2008, 19 pages.
Chilean Office Action dated Aug. 1, 2012, for Chilean Application No. 2008003779, 22 pages.
Chinese Office Action dated Mar. 28, 2012, for Chinese Application No. 200880120258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.
Japanese Office Action dated Aug. 14, 2012, for Japanese Patent Application No. 2010-538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
International Search Report dated Aug. 5, 2010, for PCT Application No. PCT/EP2010/003559, filed on Jun. 14, 2010, 10 pages.
Brorson et al., "Mutational Analysis of Avidity and Fine Specificity of Anti-Levan Antibodies," *J. Immunol.* 163:6694-6701 (1994).
Brummell et al., "Probing the combining site of an anti-carbohydrate antibody by saturation-mutagenesis: role of the heavy-chain CDR3 residues," *Biochemistry* 32(4):1180-1187 (1993).
Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.
Burks et al., "In vitro scanning saturation mutagenesis of an antibody binding pocket," *PNAS* 94(2):412-417 (1997).
Coleman., "Effects of amino acid sequence changes on antibody-antigen interactions," *Research in Immunol.* 145(1):33-38, (1994).
Dall'Acqua, W. et al. (1998). "Contribution of Domain Interface Residues to the Stability of Antibody CH3 Domain Homodimers", *Biochemistry*, 37:9266-9273.

(56) References Cited

OTHER PUBLICATIONS

Dimmock, N.J. et al. (2004). "Valency of antibody binding to virions and its determination by surface plasmon resonance", *Rev. Med. Virol.*, 14:123-135.

Dufner et al., "Harnessing phage and ribosome display for antibody optimization," *Trends Biotechol.* 24(11):523-29 (2006).

Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).

Huston, J.S. et al. (1993). "Medical Applications of Single-Chain Antibodies," *Intern. Rev. Immunol.* 10(2-3):195-217.

Jang et al., "The structural basis for DNA binding by an anti-DNA autoantibody," *Mol. Immunol.* 35(18):1207-1217 (1998).

Kobayshi et al. "Tryptophan H33 plays an important role in pyrimidine (6-4) pyrimidone photoproduct binding by a high-affinity antibody," *Protein Engineering* 12(10):879-844 (1999).

McLean, G.R. et al. (2005). "A point mutation in the CH3 domain of human IgG3 inhibits antibody secretion without affecting antigen specificity", *Molecular Immunology*, 42:1111-1119.

Mirny, L. et al. (2001). "Protein Folding Theory: From Lattice to All-Atom Models", *Annu. Rev. Biophys. Biomol. Struct.*, 30:361-96.

Novotný, J. et al. (1985). "Structural invariants of antigen binding: Comparison of immunoglobulin $V_L$ -$V_H$ and $V_L$-$V_L$ domain dimmers", *Proc. Natl. Acad. Sci. USA*, 82:4592-4596.

Pan, Q. et al. "Blocking Neuropilin-1 Function Has an Additive Effect with nti-VEGF to Ihibit Tumor Growth," *Cancer Cell* 11:53-67, (Jan. 2007).

Roitt A. et al. "Multispecific Antibodies Comprising Full Length Antibodies and Single Chain Fab Fragments," *Immunology*, English Translation, Moscow:Mir, pp. 388-389, (2000).

Stork et al. "A novel tri-functional antibody fusion protein with improved pharmacokinetic properties generated by fusing a bispecific single-chain diabody with an albumin-binding domain from streptococcal protein G," *Protein Eng. Des. Sel.* 20(11):569-576, (Nov. 2007, e-pub. Nov. 3, 2007).

Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).

Torres, M. et al. (2005). "Variable-Region-Identical Antibodies Differing in Isotype Demonstrate Differences in Fine Specificity and Idiotype", *The Journal of Immunology*, 174:2132.

Taiwanese Search Report for Taiwanese Patent Application No. 099110151, filed on Apr. 1, 2010, Completion of Search dated Sep. 12, 2012, 1 page.

Russian Office Action dated Apr. 18, 2013, for Russian Patent Application No. 2010 129 539, 3 pages.

Russian Office Action dated Oct. 8, 2014, for Russian Patent Application No. 2012 100 865, 3 pages.

Bird et al. "Single-Chain Antigen-Binding Proteins," *Science* 242(4877):423-6, (Oct. 21, 1988).

Bird et al. "Single-Chain Antigen-Binding Proteins," *Science* 244(4903):409, *Erratum*, (Apr. 28, 1989).

Brinkmann et al., "A Recombinant Immunotoxin Containing a Disulfide-Stabilized Fv Fragment," *PNAS* 90(16):7538-7542, (1993).

Huston et al. "Protein Engineering of Antibody Binding Sites: Recovery of Specific Activity in an Anti-Digoxin Single-Chain Fv Analogue Produced in *Escherichia coli,*" *Proc. Natl. Acad. Sci. U.S.A.* 85(16):5879-5883, (Aug. 1988).

Johnson et al. "Construction of Single-Chain Fv Derivatives Monoclonal Antibodies and Their Production in *Escherichia coli,*" *Methods Enzymol.* 203:88-98, (1991).

Reiter et al. "Improved Binding and Antitumor Activity of a Recombinant Anti-erbB2 Immunotoxin by Disulfide Stabilization of the Fv Fragment," *JBC* 269:18327-18331, (1994).

Reiter et al. "Engineering Interchain Disulfide Bonds into Conserved Framework Regions of Fv Fragments: Improved Biochemical Characteristics of Recombinant Immunotoxins Containing Disulfide-Stabilized Fv," *Protein Eng.* 7(5):697-704, (May 1994).

Reiter et al. "Stabilization of the Fv Fragments in Recombinant Immunotoxins by Disulfide Bonds Engineered into Conserved Framework Regions," *Biochemistry* 33:5451-5449, (1994).

Reiter et al., "Disulfide Stabilization of Antibody Fv: Computer Predictions and Experimental Evaluation," *Protein Engineering* 8:1323-1331, (1995).

Reiter et al., "Engineering Antibody Fv Fragments for Cancer Detection and Therapy: Disulfide-Stabilized Fv Fragments," *Nature Biotechnology* 14:1239-1245, (1996).

Anthony et al. (2008). "A recombinant IgG Fc that recapitulates the antiinflammatory activity of IVIG," *Science*, 320(5874):373-376.

Armour et al. (1999). "Recombinant human IgG molecules lacking Fcγ receptor I binding and monocyte triggering activities," *Eur. J. Immunol.* 29:2613-2624.

Bendig. "Humanization of Rodent Monoclonal Antibodies by CDR Grafting," *Methods: A companion to Methods in Enzymology* 8:83-93 (1995).

Carter. "Potent antibody therapeutics by design," *Nature Reviews Immunology* 6:343-357, (2006).

Chames et al. "Bispecific antibodies for cancer therapy," *Current Opinion in Drug Discovery & Development*, 12(2):276-283, (2009).

Chan et al. "Therapeutic antibodies for autoimmunity and inflammation," *Nat. Rev. Immunol.*, 10(5):301-316, (2010).

Charlton. In: Methods in Molecular Biology, vol. 248, Lo, B.K.C. (ed.), Humana Press, Totowa, NJ, pp. 245-254, (2003).

Chin et al. "Addition of p-azido-L-phenylalanine to the genetic code of *Escherichia coli,*" *J. Am. Chem. Soc.* 124(31):9026-9027, (2002).

Chin et al. "In vivo photocrosslinking with unnatural amino Acid mutagenesis," *ChemBioChem* 3(11):1135-1137, (2002).

Chin et al. "Addition of a photocrosslinking amino acid to the genetic code of *Escherichia coli,*" *Proc. Natl. Acad. Sci. U.S.A.* 99(17):11020-11024, (2002).

Clancy et al. "Sortase transpeptidases: insights into mechanism, substrate specificity, and inhibition," *Biopolymers*, 94(4):385-396, (2010).

Cruse et al. 2nd ed., CRC Press, pp. 37, 316-317, (2003).

Friend et al. "Phase I study of an engineered aglycosylated humanized CD3 antibody in renal transplant rejection," *Transplantation*, 68(11):1632-1637, (1999).

Gerngross. "Advances in the production of human therapeutic proteins in yeasts and filamentous fungi," *Nat. Biotech.* 22:1409-1414, (2004).

Greenwood et al. "Structural Motifs Involved in Human IgG Antibody Effector Functions," *Eur. J. Immunology* 23(5):1098-1104, (May 1993).

Hatfield et al. "Antiangiogenic therapy in acute myelogenous leukemia: targeting of vascular endothelial growth factor and interleukin 8 as possible antileukemic strategies," *Curr. Cancer Drug Targets*, 5(4):229-248, (2005).

Herberman. "Immunodiagnosis of Cancer", in Fleisher (ed.), "The Clinical Biochemistry of Cancer," American Association of Clinical Chemist, p. 347, (1979).

Huber et al. "Crystallographic structure studies of an IgG molecule and an Fc fragment," *Nature* 264:415-420, (1976).

Hudson et al. "Engineered antibodies," Nat. Med. 9:129-134, (2003).

Ilangovan et al. "Structure of sortase, the transpeptidase that anchors proteins to the cell wall of *Staphylococcus aureus,*" *Proc. Natl. Acad. Sci. U.S.A.* 98(11):6056-6061, (2001).

Jefferis et al. "Interaction sites on human IgG-Fc for FcγR: current models", *Immunol. Lett.*, 82:57-65, (2002).

Jiang et al. "Advances in the assessment and control of the effector functions of therapeutic antibodies," *Nat. Rev. Drug Discov.* 10(2):101-111, (2011).

Krugmann et al. " Structural Requirements for Assembly of Dimeric IgA Probed by Site-Directed Mutagenesis of J Chain and a Cysteine Residue of the α-chain CH2 Domain," *The Journal of Immunology* 159:244-249, (1997).

Levary et al. "Protein-Protein fusion catalyzed by sortase A," *PLOS One* 6:e18342.1-e18342.6, (2011).

(56) References Cited

OTHER PUBLICATIONS

Li et al. "Optimization of humanized IgGs in glycoengineered Pichia pastoris," Nat. Biotech. 24:210-215, (2006).
Madej et al. "Engineering of an anti-epidermal growth factor receptor antibody to single chain format and labeling by sortase A-mediated protein ligation," *Biotechnology and Bioengineering* 109(6):1461-1470, (2012).
Mizukami et al. "Induction of interleukin-8 preserves the angiogenic response in HIF-1alpha-deficient colon cancer cells," *Nat. Med.*, 11(9):992-997, (2005).
Möhlmann et al. "In vitro sortagging of an antibody fab fragment: overcoming unproductive reactions of sortase with water and lysine side chains," *Chembiochem: A European Journal of Chemical Biology* 12(11):1774-1780, (2011).
Noren et al. "A General Method for Site-Specific Incorporation of Unnatural Amino Acids into Proteins," *Science* 244:182-188, (1989).
Novellino et al. "A listing of human tumor antigens recognized by T cells: Mar. 2004 update," *Cancer Immunol. Immunother*, 54(3):187-207, (2005).
Parmiani et al. "Unique human tumor antigens: immunobiology and use in clinical trials," *J. Immunol*, 178(4):1975-1979, (2007).
Paul. "Structure and Function of Immunoglobulins," Chapter 9 in *Fundamental Immunology*, Third Edition, Raven Press, New York, New York, pp. 292-295, (1993).
Pleass et al. "Identification of Residues in the CH2/CH3 Domain Interface of IgA Essential for Interaction With the Human fcα Receptor (Fcα R) CD89," *The Journal of Biology Chemistry* 274(33):23508-23514, (Aug. 13, 1999).
Popp et al. "Making and breaking peptide bonds: protein engineering using sortase," *Angewandte Chemie*, 50(22):5024-5032, (2011).
Presta. "Molecular engineering and design of therapeutic antibodies," *Current Opinion in Immunology* 20:460-470, (2008).
Ren et al. "Macrophage migration inhibitory factor stimulates angiogenic factor expression and correlates with differentiation and lymph node status in patients with esophageal squamous cell carcinoma," *Ann. Surg.* 242:55-63, (2005).
Routledge et al. "The effect of aglycosylation on the immunogenicity of a humanized therapeutic CD3 monoclonal antibody," *Transplantation*, 60(8):847-853, (1995).
Roux et al. "Comparisons of the ability of human IgG3 hinge mutants, IgM, IgE, and IgA2, to form small immune complexes: a role for flexibility and geometry," *J. Immunol.*, 161(8):4083-4090, (1998).
Sakamoto et al. "Enzyme-Mediated Site-Specific Antibody-Protein Modification Using a ZZ Domain as a Linker," *BioConjugate Chem.* 21:2227-2293 (2010, e-pub. Nov. 11, 2010).
Salfeld. "Isotype Selection in Antibody Engineering," *Nat. Biotechnol.* 25(12):1369-1372, (Dec. 2007).
Sensi et al. "Unique tumor antigens: evidence for immune control of genome integrity and immunogenic targets for T cell-mediated patient-specific immunotherapy," *Clin. Cancer Res.*, 12(17):5023-5032, (2006).
Sondermann et al. "The 3.2-A crystal structure of the human IgG1 Fc fragment-FcγRIII complex", *Nature*, 406:267-273, (2000).
Strop et al. "Generating Bispecific Human IgG1 and IgG2 Antibodies from Any Antibody Pair," *Journal of Molecular Biology* 420(3):204-219, (2012).
Ta et al. "Enzymatic Single-Chain Antibody Tagging A Universal Approach to Targeted Molecular Imaging and Cell Homing in Cardiovascular Disease," *Circulation Research*, 109(4):365-373, (2011).
Thies et al. "Folding and association of the antibody domain CH3: prolyl isomerization preceeds dimerization," *J. Mol. Biol.*, 293:67-79, (1999).
Ton-That et al. "Purification and characterization of sortase, the transpeptidase that cleaves surface proteins of *Staphylococcus aureus* at the LPXTG motif," *Proc. Natl. Acad. Sci. U.S.A.*, 96(22):12424-12429, (1999).
Tsukiji et al. "Sortase-Mediated Ligation: A Gift from Gram-Positive Bacteria to Protein Engineering," *Chembiochem*, 10(5):787-798, (2009).
Vallböhmer et al. "Molecular determinants of cetuximab efficacy," *J Clin. Oncol.*, 23(15):3536-3544, (2005).
Wagner et al. "Bispecific antibody generated with sortase and click chemistry has broad antiinfluenza virus activity," *Proc. Natl. Acad. Sci. USA* 111:16820-16825, (Nov. 25, 2014).
Wang et al. "Expanding the genetic code," *Chem. Commun (Camb.)*. 7:1-11, (2002).
Ward et al. "The effector functions of immunoglobulins implications for therapy," *Ther. Immunol.* 2:77-94, (1995).
Witte et al. "Preparation of unnatural N-to-N and C-to-C protein fusions", *Proceedings of the National Academy of Sciences of the United States of America*, 109(30):11993-11998, (2012).
Yazaki et al. Methods in Molecular Biology, vol. 248, Lo, B.K.C. (ed.), Humana Press, Totawa, NJ (2004), pp. 255-268, (2004).
International Search Report dated Aug. 5, 2014, for PCT Patent Application No. PCT/EP2013/063258, filed on Jun. 25, 2013, seven pages.
Written Opinion of the International Searching Authority dated Aug. 5, 2014, for PCT Patent Application No. PCT/EP2013/063258, filed on Jun. 25, 2013, seven pages.
U.S. Appl. No. 14/551,957, filed Nov. 24, 2014 for Castoldi et al.
U.S. Appl. No. 14/579,165, filed Dec. 22, 2014, by Dieter et al.
U.S. Appl. No. 14/579,192, filed Dec. 22, 2014, by Sebastian et al.
Alt et al. "Novel Tetravalent and Bispecific IgG-Like Antibody Molecules Combining Single-Chain Diabodies With the Immunoglobulin γ1 Fc or CH3 Region," *FEBS Lett.* 454(1-2):90-94, (Jul. 2, 1999).
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering, Design & Selection* 23(4):195-202, (2010, e-pub. Feb. 4, 2010).
Metz, S. et al. "Bispecific Digoxigenin-Binding Antibodies for targeted Payload Delivery," *Proc. Natl. Acad. Sci. U.S.A.* 108 (20):8194-8199, (May 17, 2011).
Metz, S. et al. "Bispecific Antibody Derivatives with Restricted Binding Functionalities that are Activated by Proteolytic Processing," *Protein Engineering Design and Selection* 25(10):571-580, (2012, e-pub. Sep. 13, 2012).

\* cited by examiner

Fig. 1
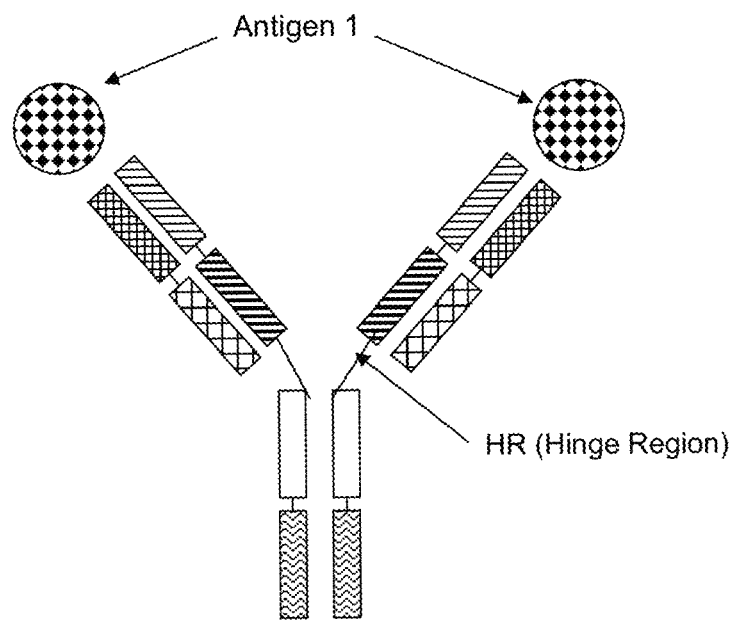
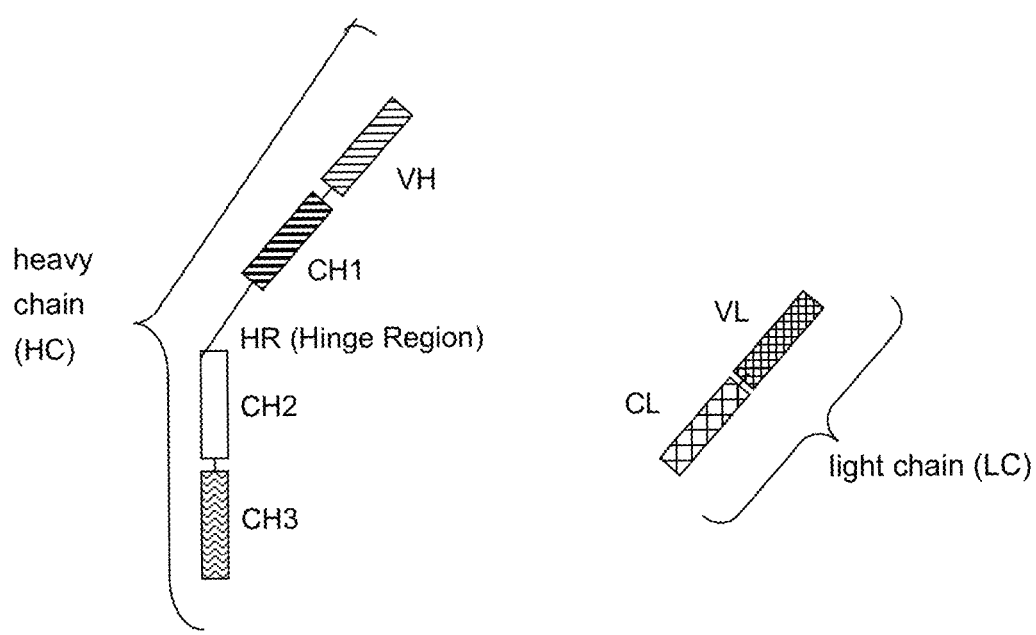
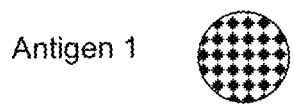

Figure 2a
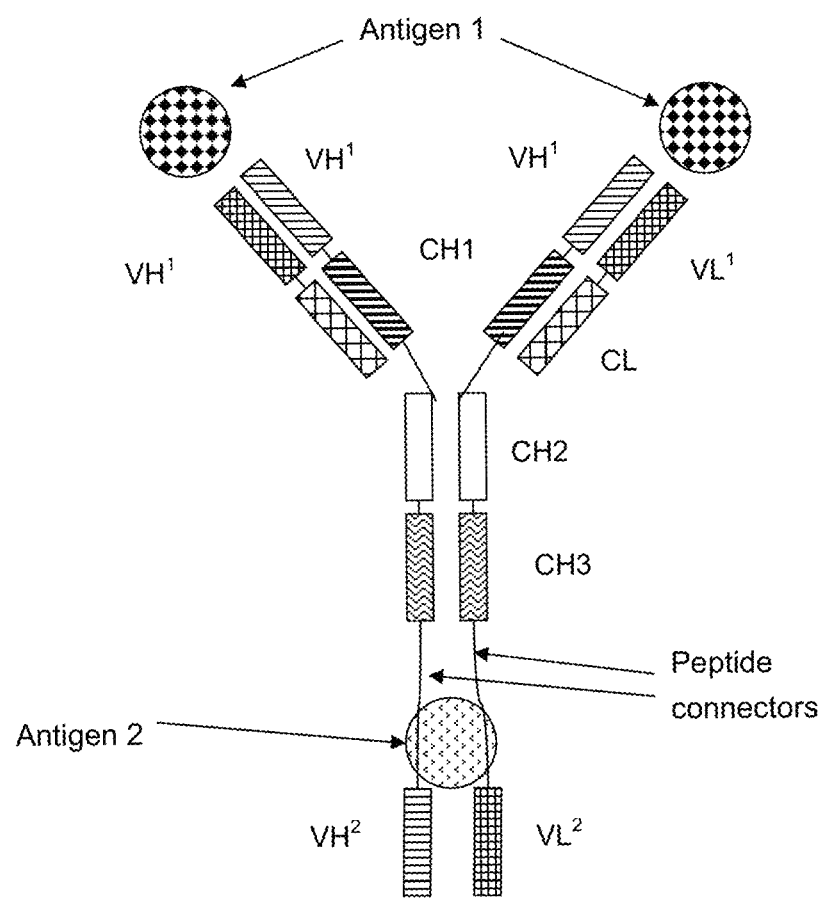

Figure 3
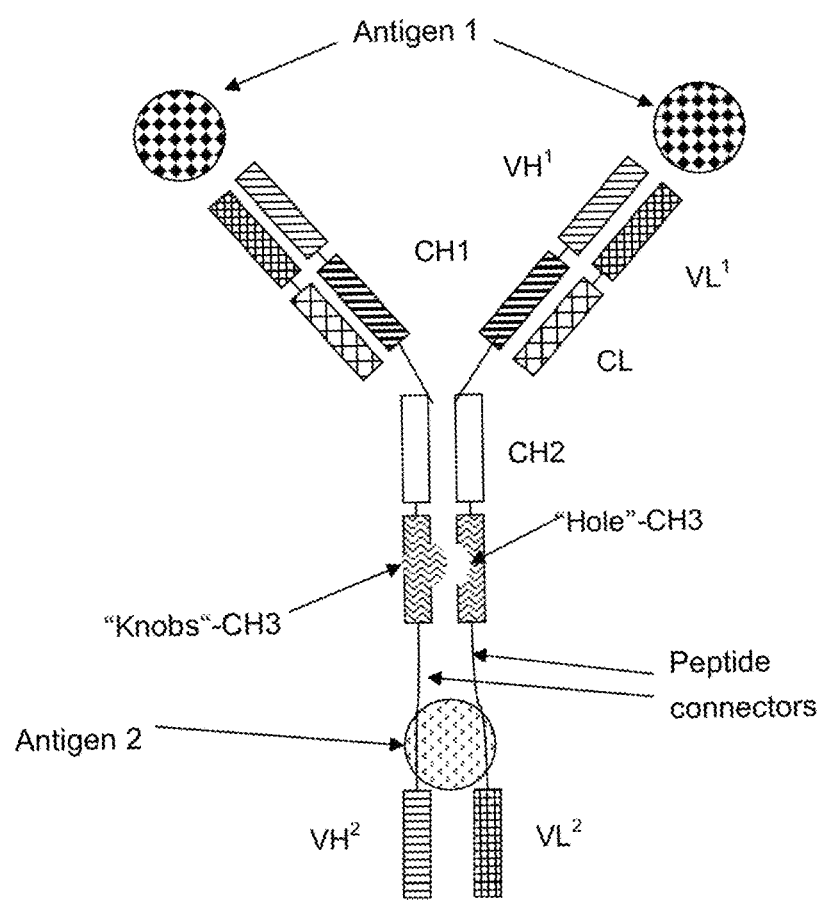
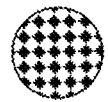

100 ng/mL HGF, cells detached

SEQUENCE LISTING

```
<160> NUMBER OF SEQ ID NOS: 37

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110
```

```
Thr Leu Thr Val Ser Ser
            115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
            115

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 4

Asp Ile Gln Met Thr Gln Ser Pro Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys

<210> SEQ ID NO 5
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Ser Asn Ser Tyr Ala Pro Ser Leu
50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser

```
                225                 230                 235                 240
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 8
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 9
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His
225

<210> SEQ ID NO 10
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 11
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Ala
             20                  25                  30

Tyr Tyr Trp Asn Trp Ile Arg Gln Phe Pro Gly Asn Lys Leu Glu Trp
         35                  40                  45

Met Gly Tyr Ile Ser Tyr Gly Gly Ser Asn Ser Tyr Ala Pro Ser Leu
 50                  55                  60

Lys Asn Arg Phe Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln

```
                165                 170                 175
Ser Ser Gly Leu Tyr Ser Leu Ser Ser Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gly Gly Gly Gly Ser Glu
450                 455                 460

Val Gln Leu Val Glu Ser Gly Gly Leu Val Gln Pro Gly Gly Ser
465                 470                 475                 480

Leu Arg Leu Ser Cys Ala Ala Ser Gly Tyr Thr Phe Thr Ser Tyr Trp
                485                 490                 495

Leu His Trp Val Arg Gln Ala Pro Gly Lys Gly Leu Glu Trp Val Gly
            500                 505                 510

Met Ile Asp Pro Ser Asn Ser Asp Thr Arg Phe Asn Pro Asn Phe Lys
            515                 520                 525

Asp Arg Phe Thr Ile Ser Ala Asp Thr Ser Lys Asn Thr Ala Tyr Leu
            530                 535                 540

Gln Met Asn Ser Leu Arg Ala Glu Asp Thr Ala Val Tyr Tyr Cys Ala
545                 550                 555                 560

Thr Tyr Arg Ser Tyr Val Thr Pro Leu Asp Tyr Trp Gly Gln Gly Thr
                565                 570                 575

Leu Val Thr Val Ser Ser
            580
```

<210> SEQ ID NO 12
<211> LENGTH: 577
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 12

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
```

```
                355                 360                 365
Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

Gly Gly Gly Gly Ser Gly Gly Gly Gly Ser Gly Gly Gly Gly Ser Asp
        450                 455                 460

Ile Gln Met Thr Gln Ser Pro Ser Ser Leu Ser Ala Ser Val Gly Asp
465                 470                 475                 480

Arg Val Thr Ile Thr Cys Lys Ser Ser Gln Ser Leu Leu Tyr Thr Ser
                485                 490                 495

Ser Gln Lys Asn Tyr Leu Ala Trp Tyr Gln Gln Lys Pro Gly Lys Ala
                500                 505                 510

Pro Lys Leu Leu Ile Tyr Trp Ala Ser Thr Arg Glu Ser Gly Val Pro
            515                 520                 525

Ser Arg Phe Ser Gly Ser Gly Ser Gly Thr Asp Phe Thr Leu Thr Ile
        530                 535                 540

Ser Ser Leu Gln Pro Glu Asp Phe Ala Thr Tyr Tyr Cys Gln Gln Tyr
545                 550                 555                 560

Tyr Ala Tyr Pro Trp Thr Phe Gly Gln Gly Thr Lys Val Glu Ile Lys
                565                 570                 575

Arg

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
                20                  25                  30

Leu Asn Trp Tyr Gln Arg Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
```

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 14
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
                20                  25                  30

Tyr Tyr Trp Asn Trp Ile Arg Gln Phe Pro Gly Asn Lys Leu Glu Trp
            35                  40                  45

Met Gly Tyr Ile Ser Tyr Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
                100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270
```

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gly Gly Gly Gly Ser Glu
    450                 455                 460

Val Gln Leu Val Glu Ser Gly Gly Gly Leu Val Gln Pro Gly Gly Ser
465                 470                 475                 480

Leu Arg Leu Ser Cys Ala Ala Ser Gly Tyr Thr Phe Thr Ser Tyr Trp
                485                 490                 495

Leu His Trp Val Arg Gln Ala Pro Gly Lys Cys Leu Glu Trp Val Gly
            500                 505                 510

Met Ile Asp Pro Ser Asn Ser Asp Thr Arg Phe Asn Pro Asn Phe Lys
        515                 520                 525

Asp Arg Phe Thr Ile Ser Ala Asp Thr Ser Lys Asn Thr Ala Tyr Leu
    530                 535                 540

Gln Met Asn Ser Leu Arg Ala Glu Asp Thr Ala Val Tyr Tyr Cys Ala
545                 550                 555                 560

Thr Tyr Arg Ser Tyr Val Thr Pro Leu Asp Tyr Trp Gly Gln Gly Thr
                565                 570                 575

Leu Val Thr Val Ser Ser
            580

<210> SEQ ID NO 15
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

-continued

```
Met Gly Tyr Ile Ser Tyr Gly Gly Ser Asn Ser Tyr Ala Pro Ser Leu
         50                  55                  60

Lys Asn Arg Phe Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                     85                  90                  95

Ala Arg Glu Ser Asp Tyr Ala Tyr Phe Asp Tyr Trp Gly Gln Gly Thr
                100                 105                 110

Thr Leu Thr Val Ser Ser Ala Ser Thr Lys Gly Pro Ser Val Phe Pro
             115                 120                 125

Leu Ala Pro Ser Ser Lys Ser Thr Ser Gly Gly Thr Ala Ala Leu Gly
         130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Ser Gly Gly Gly Gly Ser Asp
    450                 455                 460
```

```
Ile Gln Met Thr Gln Ser Pro Ser Ser Leu Ser Ala Ser Val Gly Asp
465                 470                 475                 480

Arg Val Thr Ile Thr Cys Lys Ser Gln Ser Leu Leu Tyr Thr Ser Ser
                485                 490                 495

Ser Gln Lys Asn Tyr Leu Ala Trp Tyr Gln Gln Lys Pro Gly Lys Ala
            500                 505                 510

Pro Lys Leu Leu Ile Tyr Trp Ala Ser Thr Arg Glu Ser Gly Val Pro
        515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Tyr Cys Gln Gln Tyr
545                 550                 555                 560

Tyr Ala Tyr Pro Trp Thr Phe Gly Cys Gly Thr Lys Val Glu Ile Lys
                565                 570                 575

Arg

<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 582
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gly Gly Gly Gly Ser Glu
        450                 455                 460

Val Gln Leu Val Glu Ser Gly Gly Gly Leu Val Gln Pro Gly Gly Ser
465                 470                 475                 480

Leu Arg Leu Ser Cys Ala Ala Ser Gly Tyr Thr Phe Thr Ser Tyr Trp
            485                 490                 495

Leu His Trp Val Arg Gln Ala Pro Gly Lys Cys Leu Glu Trp Val Gly
            500                 505                 510

Met Ile Asp Pro Ser Asn Ser Asp Thr Arg Phe Asn Pro Asn Phe Lys
            515                 520                 525

Asp Arg Phe Thr Ile Ser Ala Asp Thr Ser Lys Asn Thr Ala Tyr Leu
        530                 535                 540

Gln Met Asn Ser Leu Arg Ala Glu Asp Thr Ala Val Tyr Tyr Cys Ala
545                 550                 555                 560

Thr Tyr Arg Ser Tyr Val Thr Pro Leu Asp Tyr Trp Gly Gln Gly Thr
            565                 570                 575

Leu Val Thr Val Ser Ser
            580

<210> SEQ ID NO 18
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
```

-continued

```
            145                 150                 155                 160
Ser Gly Ala Leu Thr Ser Gly Val His Thr Phe Pro Ala Val Leu Gln
                    165                 170                 175
Ser Ser Gly Leu Tyr Ser Leu Ser Ser Val Val Thr Val Pro Ser Ser
                    180                 185                 190
Ser Leu Gly Thr Gln Thr Tyr Ile Cys Asn Val Asn His Lys Pro Ser
                    195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                    245                 250                 255
Thr Pro Glu Val Thr Cys Val Val Val Asp Val Ser His Glu Asp Pro
                    260                 265                 270
Glu Val Lys Phe Asn Trp Tyr Val Asp Gly Val Glu Val His Asn Ala
                    275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                    325                 330                 335
Ile Ser Lys Ala Lys Gly Gln Pro Arg Glu Pro Gln Val Cys Thr Leu
                    340                 345                 350
Pro Pro Ser Arg Asp Glu Leu Thr Lys Asn Gln Val Ser Leu Ser Cys
                    355                 360                 365
Ala Val Lys Gly Phe Tyr Pro Ser Asp Ile Ala Val Glu Trp Glu Ser
                    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Val Ser Lys Leu Thr Val Asp Lys Ser
                    405                 410                 415
Arg Trp Gln Gln Gly Asn Val Phe Ser Cys Ser Val Met His Glu Ala
                    420                 425                 430
Leu His Asn His Tyr Thr Gln Lys Ser Leu Ser Leu Ser Pro Gly Lys
                    435                 440                 445
Gly Gly Gly Gly Ser Gly Gly Gly Ser Gly Gly Gly Gly Ser Gly Asp
                    450                 455                 460
Ile Gln Met Thr Gln Ser Pro Ser Ser Leu Ser Ala Ser Val Gly Asp
465                 470                 475                 480
Arg Val Thr Ile Thr Cys Lys Ser Ser Gln Ser Leu Leu Tyr Thr Ser
                    485                 490                 495
Ser Gln Lys Asn Tyr Leu Ala Trp Tyr Gln Gln Lys Pro Gly Lys Ala
                    500                 505                 510
Pro Lys Leu Leu Ile Tyr Trp Ala Ser Thr Arg Glu Ser Gly Val Pro
                    515                 520                 525
Ser Arg Phe Ser Gly Ser Gly Ser Gly Thr Asp Phe Thr Leu Thr Ile
                    530                 535                 540
Ser Ser Leu Gln Pro Glu Asp Phe Ala Thr Tyr Tyr Cys Gln Gln Tyr
545                 550                 555                 560
Tyr Ala Tyr Pro Trp Thr Phe Gly Cys Gly Thr Lys Val Glu Ile Lys
                    565                 570                 575
```

Arg

```
<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
            85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

```
<210> SEQ ID NO 20
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20
```

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Ser Asn Ser Tyr Ala Pro Ser Leu
50                  55                  60

```
Lys Asn Arg Phe Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Glu Val Gln Leu Val Glu Ser Gly Gly Gly Leu
450                 455                 460

Val Gln Pro Gly Gly Ser Leu Arg Leu Ser Cys Ala Ala Ser Gly Tyr
465                 470                 475                 480

Thr Phe Thr Ser Tyr Trp Leu His Trp Val Arg Gln Ala Pro Gly Lys
```

```
                            485                 490                 495
Gly Leu Glu Trp Val Gly Met Ile Asp Pro Ser Asn Ser Asp Thr Arg
                500                 505                 510

Phe Asn Pro Asn Phe Lys Asp Arg Phe Thr Ile Ser Ala Asp Thr Ser
            515                 520                 525

Lys Asn Thr Ala Tyr Leu Gln Met Asn Ser Leu Arg Ala Glu Asp Thr
        530                 535                 540

Ala Val Tyr Tyr Cys Ala Thr Tyr Arg Ser Tyr Val Thr Pro Leu Asp
545                 550                 555                 560

Tyr Trp Gly Gln Gly Thr Leu Val Thr Val Ser Ser
                565                 570

<210> SEQ ID NO 21
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Asp Ile Gln Met Thr Gln Ser Pro Ser Ser Leu
    450                 455                 460

Ser Ala Ser Val Gly Asp Arg Val Thr Ile Thr Cys Lys Ser Ser Gln
465                 470                 475                 480

Ser Leu Leu Tyr Thr Ser Ser Gln Lys Asn Tyr Leu Ala Trp Tyr Gln
                485                 490                 495

Gln Lys Pro Gly Lys Ala Pro Lys Leu Leu Ile Tyr Trp Ala Ser Thr
            500                 505                 510

Arg Glu Ser Gly Val Pro Ser Arg Phe Ser Gly Ser Gly Ser Gly Thr
        515                 520                 525

Asp Phe Thr Leu Thr Ile Ser Ser Leu Gln Pro Glu Asp Phe Ala Thr
530                 535                 540

Tyr Tyr Cys Gln Gln Tyr Tyr Ala Tyr Pro Trp Thr Phe Gly Gln Gly
545                 550                 555                 560

Thr Lys Val Glu Ile Lys Arg
                565

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
                20                  25                  30

Leu Asn Trp Tyr Gln Arg Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60
```

```
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Phe Pro Trp
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
            195                 200                 205
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Ser Gly Gly Gly Gly Ser Gly
    450                 455                 460

Gly Gly Gly Ser Gly Gly Gly Gly Ser Gly Gly Gly Ser Glu Val
465                 470                 475                 480

Gln Leu Val Glu Ser Gly Gly Gly Leu Val Gln Pro Gly Gly Ser Leu
                485                 490                 495

Arg Leu Ser Cys Ala Ala Ser Gly Tyr Thr Phe Thr Ser Tyr Trp Leu
            500                 505                 510

His Trp Val Arg Gln Ala Pro Gly Lys Gly Leu Glu Trp Val Gly Met
        515                 520                 525

Ile Asp Pro Ser Asn Ser Asp Thr Arg Phe Asn Pro Asn Phe Lys Asp
        530                 535                 540

Arg Phe Thr Ile Ser Ala Asp Thr Ser Lys Asn Thr Ala Tyr Leu Gln
545                 550                 555                 560

Met Asn Ser Leu Arg Ala Glu Asp Thr Ala Val Tyr Tyr Cys Ala Thr
                565                 570                 575

Tyr Arg Ser Tyr Val Thr Pro Leu Asp Tyr Trp Gly Gln Gly Thr Leu
            580                 585                 590

Val Thr Val Ser Ser
        595

<210> SEQ ID NO 24
```

-continued

```
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
```

```
                370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

Gly Gly Gly Gly Ser Gly Gly Gly Ser Gly Gly Gly Ser Gly
450                 455                 460

Gly Gly Gly Ser Gly Gly Gly Ser Gly Gly Gly Ser Asp Ile
465                 470                 475                 480

Gln Met Thr Gln Ser Pro Ser Ser Leu Ser Ala Ser Val Gly Asp Arg
                485                 490                 495

Val Thr Ile Thr Cys Lys Ser Ser Gln Ser Leu Leu Tyr Thr Ser Ser
                500                 505                 510

Gln Lys Asn Tyr Leu Ala Trp Tyr Gln Gln Lys Pro Gly Lys Ala Pro
                515                 520                 525

Lys Leu Leu Ile Tyr Trp Ala Ser Thr Arg Glu Ser Gly Val Pro Ser
530                 535                 540

Arg Phe Ser Gly Ser Gly Ser Gly Thr Asp Phe Thr Leu Thr Ile Ser
545                 550                 555                 560

Ser Leu Gln Pro Glu Asp Phe Ala Thr Tyr Tyr Cys Gln Gln Tyr Tyr
                565                 570                 575

Ala Tyr Pro Trp Thr Phe Gly Gln Gly Thr Lys Val Glu Ile Lys Arg
                580                 585                 590

<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
                20                  25                  30

Leu Asn Trp Tyr Gln Arg Lys Pro Asp Gly Thr Val Lys Leu Leu Ile
                35                  40                  45

Tyr Tyr Thr Ser Arg Leu His Ser Gly Val Pro Ser Arg Phe Ser Gly
                50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 330
<212> TYPE: PRT
<213> ORGANISM: Homo sapiens

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 327
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 28
<211> LENGTH: 107
<212> TYPE: PRT
<213> ORGANISM: Homo sapiens

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 104
<212> TYPE: PRT
<213> ORGANISM: Homo sapiens

<400> SEQUENCE: 29

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(32)
<223> OTHER INFORMATION: This sequence may encompass 6, 7 or 8 repeating
      "GGGS" units

<400> SEQUENCE: 30

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30
```

```
<210> SEQ ID NO 31
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(32)
<223> OTHER INFORMATION: This region may encompass 6, 7 or 8 repeating
      "GGGS" units
<220> FEATURE:
<221> NAME/KEY: MOD_RES
<222> LOCATION: (33)..(35)
<223> OTHER INFORMATION: May or may not be present

<400> SEQUENCE: 31

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly
        35

<210> SEQ ID NO 32
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(35)
<223> OTHER INFORMATION: This sequence may encompass 3, 4, 5, 6 or 7
      repeating "GGGGS" units

<400> SEQUENCE: 32

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(35)
<223> OTHER INFORMATION: This region may encompass 3, 4, 5, 6 or 7
      repeating "GGGGS" units
<220> FEATURE:
<221> NAME/KEY: MOD_RES
<222> LOCATION: (36)..(38)
<223> OTHER INFORMATION: May or may not be present

<400> SEQUENCE: 33

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30
```

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Gly Ser
1               5

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Gly Trp Ser Cys Ile Ile Leu Phe Leu Val Ala Thr Ala Thr Gly
1               5                   10                  15

Val His Ser

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

TRIVALENT, BISPECIFIC ANTIBODIES

PRIORITY TO RELATED APPLICATION(S)

This application is a continuation of U.S. Ser. No. 12/752,216, filed Apr. 1, 2010, and claims the benefit of European Patent Application No. 09005108.7, filed Apr. 7, 2009, which are hereby incorporated by reference in their entirety.

SEQUENCE LISTING

The instant application contains a Sequence Listing which has been submitted via EFS-Web and is hereby incorporated by reference in its entirety. Said ASCII copy, created on Mar. 1, 2010 is named 26063.txt, and is 93,010 bytes in size.

FIELD OF THE INVENTION

The present invention relates to trivalent, bispecific antibodies, methods for their production, pharmaceutical compositions containing the antibodies, and uses thereof.

BACKGROUND OF THE INVENTION

A wide variety of multispecific recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al, Nature Biotech 23 (2005) 1126-1136; Fischer, N., and Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., and Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent $F_v$ antibody construct having at least four variable domains which are linked with each other via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking. Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

SUMMARY OF THE INVENTION

A first aspect of the current invention is a trivalent, bispecific antibody comprising
a) a full length antibody specifically binding to a first antigen and consisting of two antibody heavy chains and two antibody light chains;
b) a polypeptide consisting of
ba) an antibody heavy chain variable domain (VH); or
bb) an antibody heavy chain variable domain (VH) and an antibody constant domain 1 (CH1), wherein the polypeptide is fused with the N-terminus of the VH domain via a peptide connector to the C-terminus of one of the two heavy chains of the full length antibody
c) a polypeptide consisting of
ca) an antibody light chain variable domain (VL), or
cb) an antibody light chain variable domain (VL) and an antibody light chain constant domain (CL);
wherein the polypeptide is fused with the N-terminus of the VL domain via a peptide connector to the C-terminus of the other of the two heavy chains of the full length antibody; and wherein the antibody heavy chain variable domain (VH) of the polypeptide under b) and the antibody light chain variable domain (VL) of the polypeptide under c) together form an antigen-binding site specifically binding to a second antigen A further aspect of the invention is a nucleic acid molecule encoding a trivalent, bispecific antibody according to the invention.

Still further aspects of the invention are a pharmaceutical composition comprising the trivalent, bispecific antibody.

The trivalent, bispecific antibodies according to the invention one the one hand show new properties due to their binding to different antigens, and on the other hand are suitable for production and pharmaceutical formulation due to their stability, low aggregation and pharmacokinetic and biological properties. Due to their Ig core they still retain the properties of natural antibodies like ADCC and CDC.

DETAILED DESCRIPTION OF THE INVENTION

One aspect of the invention is trivalent, bispecific antibody comprising
a) a full length antibody specifically binding to a first antigen and consisting of two antibody heavy chains and two antibody light chains;
b) a polypeptide consisting of
ba) an antibody heavy chain variable domain (VH); or
bb) an antibody heavy chain variable domain (VH) and an antibody constant domain 1 (CH1), wherein the polypeptide is fused with the N-terminus of the VH domain via a peptide connector to the C-terminus of one of the two heavy chains of the full length antibody
c) a polypeptide consisting of
ca) an antibody light chain variable domain (VL), or
cb) an antibody light chain variable domain (VL) and an antibody light chain constant domain (CL);
wherein the polypeptide is fused with the N-terminus of the VL domain via a peptide connector to the C-terminus of the other of the two heavy chains of the full length antibody; and wherein the antibody heavy chain variable domain (VH) of the polypeptide under b) and the antibody light chain variable domain (VL) of the polypeptide under c) together form an antigen-binding site specifically binding to a second antigen Optionally the antibody heavy chain variable domain (VH) of the polypeptide under b) and the antibody light chain variable domain (VL) of the polypeptide under c) are linked and stabilized via a interchain disulfide bridge by introduction of a disulfide bond between the following positions:
i) heavy chain variable domain position 44 to light chain variable domain position 100,
ii) heavy chain variable domain position 105 to light chain variable domain position 43, or
iii) heavy chain variable domain position 101 to light chain variable domain position 100 (numbering always according to EU index of Kabat).

Techniques to introduce unnatural disulfide bridges for stabilization are described e.g. in WO 94/029350, Rajagopal, V., et al., Prot. Engin. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43. (numbering always according to EU index of Kabat) In one embodiment a trivalent, bispecific antibody without the optional disulfide stabilization between the variable domains VH and VL of the single chain Fab fragments is preferred.

The term "full length antibody" denotes an antibody consisting of two "full length antibody heavy chains" and two "full length antibody light chains" (see FIG. 1). A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE.) The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of the full length antibody denotes the last amino acid at the C-terminus of the heavy or light chain.

The N-terminus of the antibody heavy chain variable domain (VH) of the polypeptide under b) and the antibody light chain variable domain (VL) of the polypeptide under c) denotes the last amino acid at the N-terminus of VH or VL domain.

The CH3 domains of the full length antibody according to the invention can be altered by the "knob-into-holes" technology which is described in detail with several examples in e.g. WO 96/027011, Ridgway, J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech 16 (1998) 677-681; Atwell, S., et al., J. Mol. Biol. 270 (1997) 26-35) and increases the yield.

Thus in one aspect of the invention the trivalent, bispecific antibody is further is characterized in that the CH3 domain of one heavy chain of the full length antibody and the CH3 domain of the other heavy chain of the full length antibody each meet at an interface which comprises an original interface between the antibody CH3 domains;
wherein the interface is altered to promote the formation of the bivalent, bispecific antibody, wherein the alteration is characterized in that:
 a) the CH3 domain of one heavy chain is altered,
so that within the original interface the CH3 domain of one heavy chain that meets the original interface of the CH3 domain of the other heavy chain within the bivalent, bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and b) the CH3 domain of the other heavy chain is altered, so that within the original interface of the second CH3 domain that meets the original interface of the first CH3 domain within the trivalent, bispecific antibody an amino acid residue is replaced with an amino acid residue having a smaller side chain volume, thereby generating a cavity within the interface of the second CH3 domain within which a protuberance within the interface of the first CH3 domain is positionable.

Preferably the amino acid residue having a larger side chain volume is selected from the group consisting of arginine (R), phenylalanine (F), tyrosine (Y), tryptophan (W).

Preferably the amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In a preferred embodiment, the trivalent, bispecific comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M., et al., Nature Biotech 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the trivalent, bispecific antibody comprises Y349C, T366W mutations in one of the two CH3 domains and E356C, T366S, L368A, Y407V mutations in the other of the two CH3 domains or the trivalent, bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat). But also other knobs-in-holes technologies as described by EP 1 870 459A1, can be used alternatively or additionally. A preferred example for the trivalent, bispecific antibody are R409D; K370E mutations in the CH3 domain of the "knobs chain" and D399K; E357K mutations in the CH3 domain of the "hole chain" (numbering always according to EU index of Kabat).

In another preferred embodiment the trivalent, bispecific antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another preferred embodiment the trivalent, bispecific antibody comprises Y349C, T366W mutations in one of the two CH3 domains and S354C, T366S, L368A, Y407V mutations in the other of the two CH3 domains or the trivalent, bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

The bispecific antibody to the invention comprises three antigen-binding sites (A) the full length antibody according comprises two identical antigen-binding sites specifically binding to a first antigen, and B) the antibody heavy chain variable domain (VH) of the polypeptide under b) and the antibody light chain variable domain (VL) of the polypeptide under c) form together one antigen binding site specifically binding to a second antigen). The terms "binding site" or "antigen-binding site" as used herein denotes the region(s) of the bispecific antibody according to the invention to which the respective antigen actually specifically binds. The antigen binding sites either in the full length antibody or by the antibody heavy chain variable domain (VH) of the polypeptide under b) and the antibody light chain variable domain (VL) of the polypeptide under c) are formed each by a pair consisting of an antibody light chain variable domain (VL) and an antibody heavy chain variable domain (VH).

The antigen-binding sites that specifically bind to the desired antigen can be derived a) from known antibodies to the antigen or b) from new antibodies or antibody fragments obtained by de novo immunization methods using inter alia either the antigen protein or nucleic acid or fragments thereof or by phage display.

An antigen-binding site of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. "Bispecific antibodies" according to the invention are antibodies which have two different antigen-binding specificities. Where an antibody has more than one specificity, the recognized epitopes may be associated with a single antigen or with more than one antigen. The term "monospecific" antibody as used herein denotes an antibody that has one or more binding sites each of which bind to the same epitope of the same antigen. The term "valent" as used within the current application denotes the presence of a specified number of binding sites in an antibody molecule. A natural antibody for example or a full length antibody according to the invention has two binding sites and is bivalent. As such, the terms "trivalent", denote the presence of three binding sites in an antibody molecule. The bispecific antibodies according to the invention are "trivalent". The term "trivalent, bispecific" antibody as used herein denotes an antibody that has three antigen-binding sites of which two bind to the same antigen (or the same epitope of the antigen) and the third binds to a different antigen or a different epitope of the same antigen. Antibodies of the present invention have three binding sites and are bispecific.

Another embodiment of the current invention is a trivalent, bispecific antibody comprising:

a) a full length antibody specifically binding to a first antigen and consisting of:

aa) two antibody heavy chains consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3); and ab) two antibody light chains consisting in N-terminal to C-terminal direction of an antibody light chain variable domain (VL), and an antibody light chain constant domain (CL); and
b) a polypeptide consisting of
ba) an antibody heavy chain variable domain (VH); or
bb) an antibody heavy chain variable domain (VH) and an antibody constant domain 1 (CH1), wherein the polypeptide is fused with the N-terminus of the VH domain via a peptide connector to the C-terminus of one of the two heavy chains of the full length antibody wherein the peptide connector is a peptide of at least 5 amino acids, preferably between 25 and 50 amino acids;
c) a polypeptide consisting of
ca) an antibody light chain variable domain (VL), or
cb) an antibody light chain variable domain (VL) and an antibody light chain constant domain (CL);
wherein the polypeptide is fused with the N-terminus of the VL domain via a peptide connector to the C-terminus of the other of the two heavy chains of the full length antibody;
wherein the peptide connector is identical to the peptide connector under b);
and wherein the antibody heavy chain variable domain (VH) of the polypeptide under b) and the antibody light chain variable domain (VL) of the polypeptide under c) together form an antigen-binding site specifically binding to a second antigen.

Within this embodiment, preferably the trivalent, bispecific antibody comprises a T366W mutation in one of the two CH3 domains of and T366S, L368A, Y407V mutations in the other of the two CH3 domains and more preferably the trivalent, bispecific antibody comprises Y349C, T366W mutations in one of the two CH3 domains of and D356C, T366S, L368A, Y407V mutations in the other of the two CH3 domains (the additional Y349C mutation in one CH3 domain and the additional D356C mutation in the other CH3 domain forming a interchain disulfide bridge).

In one embodiment of the invention the trivalent, bispecific antibody according to the invention is characterized in that
a) the full length antibody is specifically binding to ErbB-3 comprises as heavy chain variable domain the sequence of SEQ ID NO: 1, and as light chain variable domain the sequence of SEQ ID NO: 2
b) the polypeptide under b) comprises as the heavy chain variable domain the sequence of SEQ ID NO: 3; and
c) the polypeptide under c) comprises as the light chain variable domain the sequence of SEQ ID NO: 4.

In another aspect of the current invention the trivalent, bispecific antibody according to the invention comprises
a) a full length antibody binding to a first antigen consisting of two antibody heavy chains VH-CH1-HR-CH2-CH3 and two antibody light chains VL-CL;
(wherein preferably one of the two CH3 domains comprises Y349C, T366W mutations and the other of the two CH3 domains comprises S354C, T366S, L368A, Y407V mutations);
b) a polypeptide consisting of
ba) an antibody heavy chain variable domain (VH); or
bb) an antibody heavy chain variable domain (VH) and an antibody constant domain 1 (CH1), wherein the polypeptide is fused with the N-terminus of the VH domain via a peptide connector to the C-terminus of one of the two heavy chains of the full length antibody
c) a polypeptide consisting of
ca) an antibody light chain variable domain (VL), or
cb) an antibody light chain variable domain (VL) and an antibody light chain constant domain (CL);
wherein the polypeptide is fused with the N-terminus of the VL domain via a peptide connector to the C-terminus of the other of the two heavy chains of the full length antibody;
and wherein the antibody heavy chain variable domain (VH) of the polypeptide under b) and the antibody light chain variable domain (VL) of the polypeptide under c) together form an antigen-binding site specifically binding to a second antigen.

Another embodiment of the current invention is a trivalent, bispecific antibody comprising
a) a full length antibody specifically binding to human ErbB-3 and consisting of:
aa) two antibody heavy chains consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3); and
ab) two antibody light chains consisting in N-terminal to C-terminal direction of an antibody light chain variable domain (VL), and an antibody light chain constant domain (CL) (VL-CL); and
b) one single chain Fv fragment specifically binding to human c-Met),
wherein the single chain Fv fragment under b) is fused to the full length antibody under a) via a peptide connector at the C- or N-terminus of the heavy or light chain (preferably at the C-terminus of the heavy chain) of the full length antibody;
wherein the peptide connector is a peptide of at least 5 amino acids, preferably between 25 and 50 amino acids.

Preferably such trivalent, bispecific antibody further comprises Y349C, T366W mutations in one of the two CH3 domains of the full length antibody and S354C (or E356C), T366S, L368A, Y407V mutations in the other of the two CH3 domains of the full length antibody.

Another embodiment of the current invention is a trivalent, bispecific antibody comprising
a) a full length antibody specifically binding to human ErbB-3 and consisting of:
aa) two antibody heavy chains consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3); and
ab) two antibody light chains consisting in N-terminal to C-terminal direction of an antibody light chain variable domain (VL), and an antibody light chain constant domain (CL); and
b) a polypeptide consisting of
ba) an antibody heavy chain variable domain (VH); or
bb) an antibody heavy chain variable domain (VH) and an antibody constant domain 1 (CH1), wherein the polypeptide is fused with the N-terminus of the VH domain via a peptide connector to the C-terminus of one of the two heavy chains of the full length antibody wherein the peptide connector is a peptide of at least 5 amino acids, preferably between 25 and 50 amino acids;
c) a polypeptide consisting of
ca) an antibody light chain variable domain (VL), or
cb) an antibody light chain variable domain (VL) and an antibody light chain constant domain (CL);
wherein the polypeptide is fused with the N-terminus of the VL domain via a peptide connector to the C-terminus of the other of the two heavy chains of the full length antibody;

wherein the peptide connector is identical to the peptide connector under b);
and wherein the antibody heavy chain variable domain (VH) of the polypeptide under b) and the antibody light chain variable domain (VL) of the polypeptide under c) together form an antigen-binding site specifically binding to human c-Met The full length antibodies of the invention comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, a full length antibody of the invention has a constant domain structure of an IgG type antibody.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202, 238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brüggemann, M., et al., Year Immunol. 7 (1993) 33-40). Human antibodies can also be produced in phage display libraries (Hoogenboom, H. R., and Winter, G. J., Mol. Biol. 227 (1992) 381-388; Marks, J. D., et al., J. Mol. Biol. 222 (1991) 581-597). The techniques of Cole, S. P. C., et al., and Boerner, P., et al., are also available for the preparation of human monoclonal antibodies (Cole, S. P. C., et al., Monoclonal Antibodies and Cancer Therapy, Alan R. Liss, p. 77-96 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, E. A., et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of the antigen in an in vitro assay, preferably in an plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity ($K_D$) of $10^{-8}$ mol/l or less, preferably $10^{-9}$ M to $10^{-13}$ mol/l. Thus, an trivalent, bispecific antibody according to the invention is specifically binding to each antigen for which it is specific with a binding affinity ($K_D$) of $10^{-8}$ mol/l or less, preferably $10^{-9}$ M to $10^{-13}$ mol/l.

Binding of the antibody to the FcγRIII can be investigated by a BIAcore assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is the to specifically bind an antigen when it preferentially recognizes its target antigen in a complex mixture of proteins and/or macromolecules.

The term "peptide connector" as used within the invention denotes a peptide with amino acid sequences, which is preferably of synthetic origin. These peptide connectors according to invention are used to fuse the polypeptides under b) and c) to the heavy chain C-termini of the full length antibody to form the trivalent, bispecific antibody according to the invention. Preferably the peptide connectors are peptides with an amino acid sequence with a length of at least 5 amino acids, preferably with a length of 10 to 100 amino acids, more preferably with a length of 25 to 50 amino acids. Preferably the peptide connector under b) and c) are identical peptides with a length of at least 25 amino acids, preferably with a length between 25 and 50 amino acids and more preferably the peptide connector is (G×S)n or (G×S)nGm with G=glycine, S=serine, and (x=3, n=6, 7 or 8, and m=0, 1, 2 or 3) or (x=4, n=3, 4, 5, 6, or 7 and m=0, 1, 2 or 3), preferably x=4 and n=5, 6, or 7.

In a further embodiment the trivalent, bispecific antibody according to the invention is characterized in that the full length antibody is of human IgG1 subclass, or of human IgG1 subclass with the mutations L234A and L235A.

In a further embodiment the trivalent, bispecific antibody according to the invention is characterized in that the full length antibody is of human IgG2 subclass.

In a further embodiment the trivalent, bispecific antibody according to the invention is characterized in that the full length antibody is of human IgG3 subclass.

In a further embodiment the trivalent, bispecific antibody according to the invention is characterized in that the full length antibody is of human IgG4 subclass or, of human IgG4 subclass with the additional mutation S228P.

Preferably the trivalent, bispecific antibody according to the invention is characterized in that the full length antibody is of human IgG1 subclass, of human IgG4 subclass with the additional mutation S228P.

It has now been found that the trivalent, bispecific antibodies according to the invention have improved characteristics such as biological or pharmacological activity, pharmacokinetic properties or toxicity. They can be used e.g. for the treatment of diseases such as cancer.

In a further embodiment the trivalent, bispecific antibody according to the invention is characterized in specifically binding to ErbB3 and c-Met. The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G., and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies are reported e.g. in WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835, WO 2000/061739.

Surprisingly the bispecific <ErbB3-c-Met> antibodies which are one embodiment of the invention show reduced downregulation and internalization of target antigen compared to their parent <ErbB3> and/or <c-Met> antibodies. Therefore in one preferred embodiment of the invention, the bispecific antibody is glycosylated (if it comprises an Fc part of IgG1, IgG2, IgG3 or IgG4 subclass, preferably of IgG1 or IgG3 subclass) with a sugar chain at Asn297 whereby the amount of fucose within the sugar chain is 65% or lower (Numbering according to Kabat). In another embodiment is the amount of fucose within the sugar chain is between 5% and 65%, preferably between 20% and 40%. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. In one embodiment the glycosylated antibody according to the invention the IgG subclass is of human IgG1 subclass, of human IgG1 subclass with the mutations L234A and L235A or of IgG3 subclass. In a further embodiment the amount of N-glycolylneuraminic acid (NGNA) is 1% or less and/or the amount of N-terminal alpha-1,3-galactose is 1% or less within the sugar chain. The sugar chain show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E. A., et al., Sequences of Proteins of Immunological Interest, 5th Ed. Public Health Service, National Institutes of Health, Bethesda, Md. (1991), and by Brüggemann, M., et al., J. Exp. Med. 166 (1987) 1351-1361; Love, T. W., et al., Methods Enzymol. 178 (1989) 515-527. These structures are designated as G0, G1 (α-1,6- or α-1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glyco-modified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of the sugar within the sugar chain at Asn297, related to the sum of all glycostructures attached to Asn297 (e.g. complex, hybrid and high mannose structures) measured by MALDI-TOF mass spectrometry and calculated as average value. The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibody according to the invention is produced by recombinant means. Thus, one aspect of the current invention is a nucleic acid encoding the antibody according to the invention and a further aspect is a cell comprising the nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The trivalent, bispecific antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the trivalent, bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the trivalent, bispecific antibody according to the invention for the treatment of cancer.

Another aspect of the invention is the pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and van der Eb, A. J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S. N, et al., PNAS 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

Description of the Amino Acid Sequences

SEQ ID NO:1 heavy chain variable domain <ErbB3> HER3 clone 29
SEQ ID NO:2 light chain variable domain <ErbB3> HER3 clone 29
SEQ ID NO:3 heavy chain variable domain <c-Met> Mab 5D5
SEQ ID NO:4 light chain variable domain <c-Met> Mab 5D5
SEQ ID NO:5 heavy chain <ErbB3> HER3 clone 29
SEQ ID NO:6 light chain <ErbB3> HER3 clone 29
SEQ ID NO:7 heavy chain <c-Met> Mab 5D5
SEQ ID NO:8 light chain <c-Met> Mab 5D5
SEQ ID NO:9 heavy chain <c-Met> Fab 5D5
SEQ ID NO:10 light chain <c-Met> Fab 5D5
SEQ ID NO:11 heavy chain 1 <ErbB3-c-Met> Her3/Met_KHSS
SEQ ID NO:12 heavy chain 2 <ErbB3-c-Met> Her3/Met_KHSS
SEQ ID NO:13 light chain <ErbB3-c-Met> Her3/Met_KHSS
SEQ ID NO:14 heavy chain 1 <ErbB3-c-Met> Her3/Met_SSKH
SEQ ID NO:15 heavy chain 2 <ErbB3-c-Met> Her3/Met_SSKH
SEQ ID NO:16 light chain <ErbB3-c-Met> Her3/Met_SSKH
SEQ ID NO:17 heavy chain 1 <ErbB3-c-Met> Her3/Met_SSKHSS
SEQ ID NO:18 heavy chain 2 <ErbB3-c-Met> Her3/Met_SSKHSS
SEQ ID NO:19 light chain <ErbB3-c-Met> Her3/Met_SSKHSS
SEQ ID NO:20 heavy chain 1 <ErbB3-c-Met> Her3/Met_1C
SEQ ID NO:21 heavy chain 2 <ErbB3-c-Met> Her3/Met_1C
SEQ ID NO:22 light chain <ErbB3-c-Met> Her3/Met_1C
SEQ ID NO:23 heavy chain 1 <ErbB3-c-Met> Her3/Met_6C
SEQ ID NO:24 heavy chain 2 <ErbB3-c-Met> Her3/Met_6C
SEQ ID NO:25 light chain <ErbB3-c-Met> Her3/Met_6C
SEQ ID NO:26 heavy chain constant region of human IgG1
SEQ ID NO:27 heavy chain constant region of human IgG1
SEQ ID NO:28 human light chain kappa constant region
SEQ ID NO:29 human light chain lambda constant region The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1 Schematic structure of a full length antibody without CH4 domain specifically binding to a first antigen 1 with two pairs of heavy and light chain which comprise variable and constant domains in a typical order.

FIG. 3 Schematic representation of a trivalent, bispecific antibody according to the invention, comprising a full length antibody specifically binding to a first antigen 1 to which two polypeptides VH and VL are fused (the VH and VL domains of both together forming a antigen binding site specifically binding to a second antigen 2) with "knobs and holes".

EXPERIMENTAL PROCEDURE

Examples

Materials & Methods

Recombinant DNA Techniques

Figure 2B:
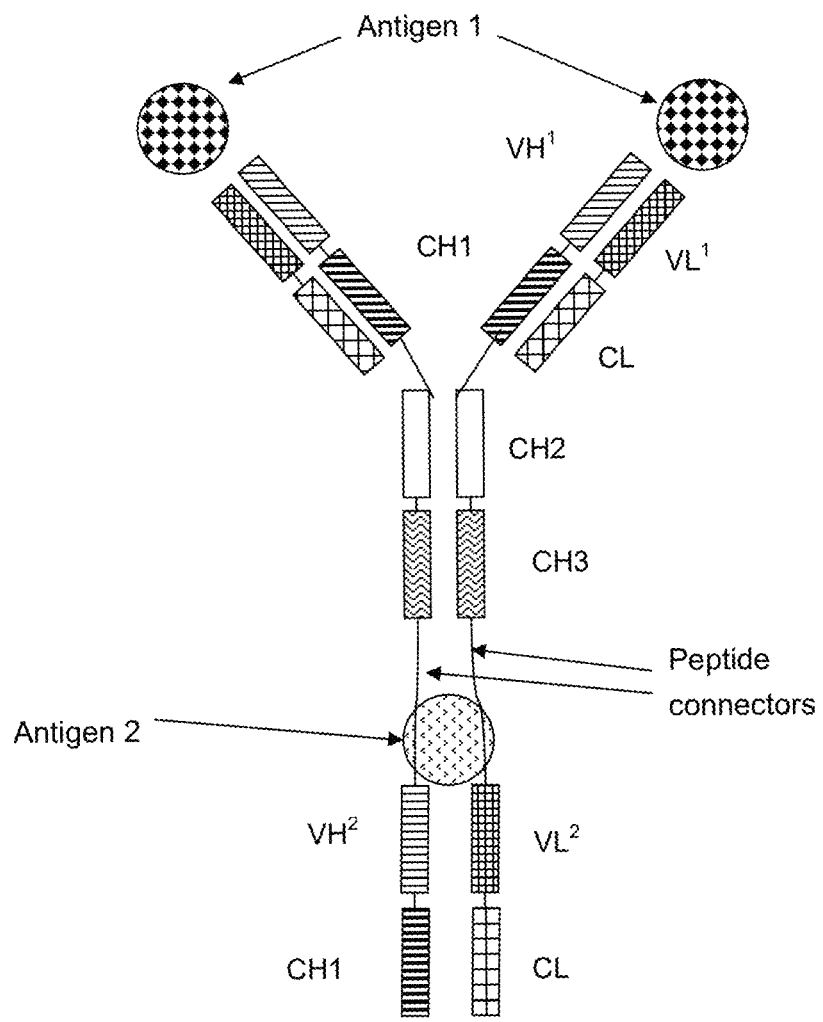
FIG. 2 Schematic representation of a trivalent, bispecific antibody according to the invention, comprising a full length antibody specifically binding to a first antigen 1 to which
a) FIG. 2a two polypeptides VH and VL are fused (the VH and VL domains of both together forming a antigen binding site specifically binding to a second antigen 2;
b) FIG. 2b two polypeptides VH-CH1 and VL-CL are fused (the VH and VL domains of both together forming a antigen binding site specifically binding to a second antigen 2)
Figure 4:
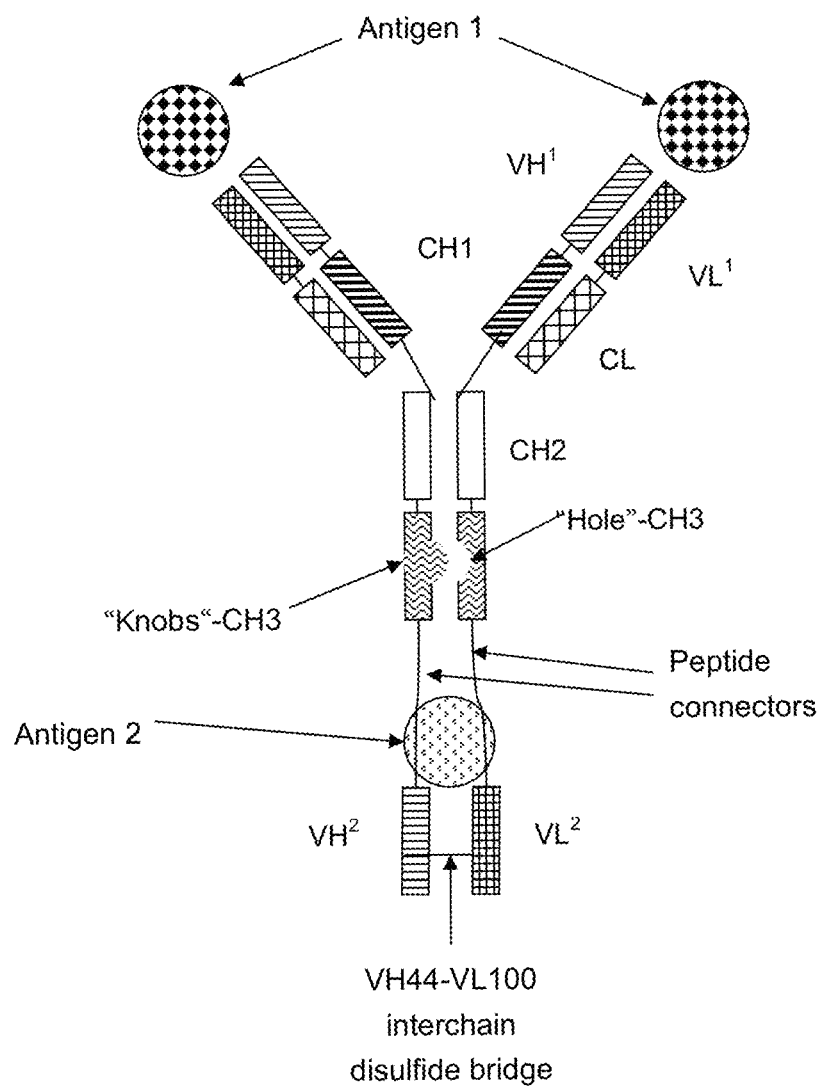
FIG. 4 Schematic representation of a trivalent, bispecific antibody according to the invention, comprising a full length antibody specifically binding to a first antigen 1 to which two polypeptides VH and VL are fused (the VH and VL domains of both together forming a antigen binding site specifically binding to a second antigen 2, wherein these VH and VL domains comprise an interchain disulfide bridge between positions VH44 and VL100) with "knobs and holes".

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing. Gene Segments coding "knobs-into-hole" Her3 (clone 29) antibody heavy chain carrying a T366W mutation in the CH3 domain with a C-terminal 5D5 VH region linked by a $(G_4S)_n$ peptide connector as well as "knobs-into-hole" Her3 (clone 29) antibody heavy chain carrying T366S, L368A and Y407V mutations with a C-terminal 5D5 VL region linked by a $(G_4S)_n$ peptide connector were synthesized with 5'-BamHI and 3'-XbaI restriction sites. In a similar manner, DNA sequences coding "knobs-into-hole" Her3 (clone 29) antibody heavy chain carrying S354C and T366W mutations in the CH3 domain with a C-terminal 5D5 VH region linked by a $(G_4S)_n$ peptide connector as well as "knobs-into-hole" Her3 (clone 29) antibody heavy chain carrying Y349C, T366S, L368A and Y407V mutations with a C-terminal 5D5 VL region linked by a $(G_4S)_n$ peptide connector were prepared by gene synthesis with flanking BamHI and XbaI restriction sites. Finally, DNA sequences encoding unmodified heavy and light chains of the Her3 (clone 29) and 5D5 antibody were synthesized with flanking BamHI and XbaI restriction sites. All constructs were designed with a 5'-end DNA sequence coding for a leader peptide (MGWSCIIL-FLVATATGVHS), which targets proteins for secretion in eukaryotic cells.

Construction of the Expression Plasmids

A Roche expression vector was used for the construction of all heavy VH/or VL fusion protein and light chain protein encoding expression plasmids. The vector is composed of the following elements:

- a hygromycin resistance gene as a selection marker,
- an origin of replication, oriP, of Epstein-Barr virus (EBV),
- an origin of replication from the vector pUC18 which allows replication of this plasmid in E. coli
- a beta-lactamase gene which confers ampicillin resistance in E. coli,
- the immediate early enhancer and promoter from the human cytomegalovirus (HCMV),
- the human 1-immunoglobulin polyadenylation ("poly A") signal sequence, and
- unique BamHI and XbaI restriction sites.

The immunoglobulin fusion genes comprising the heavy or light chain constructs as well as "knobs-into-hole" constructs with C-terminal VH and VL domains were prepared by gene synthesis and cloned into pGA18 (ampR) plasmids as described. The pG18 (ampR) plasmids carrying the synthesized DNA segments and the Roche expression vector were digested with BamHI and XbaI restriction enzymes (Roche Molecular Biochemicals) and subjected to agarose gel electrophoresis. Purified heavy and light chain coding DNA segments were then ligated to the isolated Roche expression vector BamHI/XbaI fragment resulting in the final expression vectors. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2\times10^6$ viable cells/ml on the day of transfection. DNA-293Fectin™ complexes were prepared in Opti-MEM® I medium (Invitrogen, USA) using 325 µl of 293Fectin™ (Invitrogen, Germany) and 250 µg of heavy and light chain plasmid DNA in a 1:1 molar ratio for a 250 ml final transfection volume. "Knobs-into-hole" DNA-293fectin complexes were prepared in Opti-MEM® I medium (Invitrogen, USA) using 325 µl of 293Fectin™ (Invitrogen, Germany) and 250 µg of "Knobs-into-hole" heavy chain 1 and 2 and light chain plasmid DNA in a 1:1:2 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

Purification of Trivalent Bispecific and Control Antibodies

Trivalent bispecific and control antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Fractions containing purified bispecific and control antibodies with less than 5% high molecular weight aggregates were pooled and stored as 1.0 mg/ml aliquots at −80° C. Fab fragments were generated by a Papain digest of the purified 5D5 monoclonal antibody and subsequent removal of contaminating Fc domains by Protein A chromatography. Unbound Fab fragments were further purified on a Superdex200 HiLoad 120 ml 16/60 gel filtration column (GE Healthcare, Sweden) equilibrated with 20 mM Histidin, 140 mM NaCl, pH 6.0, pooled and stored as 1.0 mg/ml aliquots at −80° C.

Analysis of Purified Proteins

The protein concentration of purified protein samples was determined by measuring the optical density (OD) at 280 nm, using the molar extinction coefficient calculated on the basis of the amino acid sequence. Purity and molecular weight of bispecific and control antibodies were analyzed by SDS-PAGE in the presence and absence of a reducing agent (5 mM 1,4-dithiotreitol) and staining with Coomassie brilliant blue). The NuPAGE® Pre-Cast gel system (Invitrogen, USA) was used according to the manufacturer's instruction (4-20% Tris-Glycine gels). The aggregate content of bispecific and control antibody samples was analyzed by high-performance SEC using a Superdex 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes. For stability analysis, concentrations of 1 mg/ml of purified proteins were incubated at 4° C. and 40° C. for 7 days and then evaluated by high-performance SEC. The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

c-Met Phosphorylation Assay

5×10e5 A549 cells were seeded per well of a 6-well plate the day prior HGF stimulation in RPMI with 0.5% FCS (fetal calf serum). The next day, growth medium was replaced for one hour with RPMI containing 0.2% BSA (bovine serum albumine). 5 µg/mL of the bispecific antibody was then added to the medium and cells were incubated for 10 minutes upon which HGF was added for further 10 minutes in a final concentration of 50 ng/mL. Cells were washed once with ice cold PBS containing 1 mM sodium vanadate upon which they were placed on ice and lysed in the cell culture plate with 100 µL lysis buffer (50 mM Tris-Cl pH7.5, 150 mM NaCl, 1% NP40, 0.5% DOC, aprotinine, 0.5 mM PMSF, 1 mM sodium-vanadate). Cell lysates were transferred to eppendorf tubes and lysis was allowed to proceed for 30 minutes on ice. Protein concentration was determined using the BCA method (Pierce). 30-50 µg of the lysate was separated on a 4-12% Bis-Tris NuPage gel (Invitrogen) and proteins on the gel were transferred to a nitrocellulose membrane. Membranes were blocked for one hour with TBS-T containing 5% BSA and developed with a phospho-specific c-Met antibody directed against Y1230, 1234, 1235 (44-888, Biosource) according to the manufacturer's instructions. Immunoblots were reprobed with an antibody binding to unphosphorylated c-Met (AF276, R&D).

Her3 (ErbB3) Phosphorylation Assay

2×10e5 MCF7 cells were seeded per well of a 12-well plate in complete growth medium (RPMI 1640, 10% FCS). Cells were allowed to grow to 90% confluency within two days. Medium was then replaced with starvation medium containing 0.5% FCS. The next day the respective antibodies were supplemented at the indicated concentrations 1 hour prior addition of 500 ng/mL Heregulin (R&D). Upon addition of Heregulin cells were cultivated further 10 minutes before the cells were harvested and lysed. Protein concentration was determined using the BCA method (Pierce). 30-50 µg of the lysate was separated on a 4-12% Bis-Tris NuPage gel (Invitrogen) and proteins on the gel were transferred to a nitrocellulose membrane. Membranes were blocked for one hour with TBS-T containing 5% BSA and developed with a phospho-specific Her3/ErbB3 antibody specifically recognizing Tyr1289 (4791, Cell Signaling).

Scatter Assay

A549 (4000 cells per well) or A431 (8000 cells per well) were seeded the day prior compound treatment in a total volume of 200 µL in 96-well E-Plates (Roche, 05232368001) in RPMI with 0.5% FCS. Adhesion and cell growth was monitored over night with the Real Time Cell Analyzer machine with sweeps every 15 min monitoring the impedance. The next day, cells were pre-incubated with 5 µL of the respective antibody dilutions in PBS with sweeps every five minutes. After 30 minutes 2.5 µL of a HGF solution yielding a final concentration of 20 ng/mL were added and the experiment was allowed to proceed for further 72 hours. Immediate changes were monitored with sweeps every minute for 180 minutes followed by sweeps every 15 minutes for the remainder of the time.

FACS a) Binding Assay

A431 were detached and counted. 1.5×10e5 cells were seeded per well of a conical 96-well plate. Cells were spun down (1500 rpm, 4° C., 5 min) and incubated for 30 min on ice in 50 µL of a dilution series of the respective bispecific antibody in PBS with 2% FCS (fetal calf serum). Cells were again spun down and washed once with 200 µL PBS containing 2% FCS followed by a second incubation of 30 min with a phycoerythrin-coupled antibody directed against human Fc which was diluted in PBS containing 2% FCS (Jackson Immunoresearch, 109116098). Cells were spun down washed twice with 200 µL PBS containing 2% FCS, resuspended in BD CellFix solution (BD Biosciences) and incubated for at least 10 min on ice. Mean fluorescence intensity (mfi) of the cells was determined by flow cytometry (FACS Canto, BD). Mfi was determined at least in duplicates of two independent stainings Flow cytometry spectra were further processed using the FlowJo software (TreeStar). Half-maximal binding was determined using XLFit 4.0 (IDBS) and the dose response one site model 205.

b) Internalization Assay

Cells were detached and counted. 5×10e5 cells were placed in 50 µL complete medium in an eppendorf tube and incubated with 5 µg/mL of the respective bispecific antibody at 37° C. After the indicated time points cells were stored on ice until the time course was completed. Afterwards, cells were transferred to FACS tubes, spun down (1500 rpm, 4° C., 5 min), washed with PBS+2% FCS and incubated for 30 minutes in 50 µL phycoerythrin-coupled secondary antibody directed against human Fc which was diluted in PBS containing 2% FCS (Jackson Immunoresearch, 109116098). Cells were again spun down, washed with PBS+2% FCS and fluorescence intensity was determined by flow cytometry (FACS Canto, BD).

c) Crosslinking Experiment

HT29 cells were detached counted and split in two populations which were individually stained with PKH26 and PKH67 (Sigma) according to the manufacturer's instructions. Of each of the stained populations 5×10e5 cells were taken, combined and incubated for 30 and 60 minutes with 10 μg/mL of the respective bispecific antibody in complete medium. After the indicated time points cells were stored on ice until the time course was completed. Cells were spun down (1500 rpm, 4° C., 5 min), washed with PBS+2% FCS and fluorescence intensity was determined by flow cytometry (FACS Canto, BD).

Cell Titer Glow Assay

Cell viability and proliferation was quantified using the cell titer glow assay (Promega). The assay was performed according to the manufacturer's instructions. Briefly, cells were cultured in 96-well plates in a total volume of 100 μL for the desired period of time. For the proliferation assay, cells were removed from the incubator and placed at room temperature for 30 min. 100 μL of cell titer glow reagent were added and multi-well plates were placed on an orbital shaker for 2 min. Luminescence was quantified after 15 min on a microplate reader (Tecan).

Wst-1 Assay

A Wst-1 viability and cell proliferation assay was performed as endpoint analysis, detecting the number of metabolic active cells. Briefly, 20 μL of Wst-1 reagent (Roche, 11644807001) were added to 200 μL of culture medium. 96-well plates were further incubated for 30 min to 1 h until robust development of the dye. Staining intensity was quantified on a microplate reader (Tecan) at a wavelength of 450 nm.

Design of Expressed and Purified Trivalent, Bispecific <ErbB3-c-Met> Antibodies

In Table 1: Trivalent, bispecific <ErbB3-c-Met> antibodies based on a full length ErbB-3 antibody (HER3 clone29) and the VH and VL domain from a C-met antibody (c-Met 5D5) with the respective features shown in Table1 one were expressed and purified according to the general methods described above. The corresponding VH and VL of HER3 clone29 and c-Met 5D5 are given in the sequence listing.

TABLE 1

Trivalent, bispecific antibody < ErbB3-c-Met> with the VHVL-Ab-nomenclature in Table 1 were expressed and purified (see also in the Examples below and FIG. 3c)

| Features: | Her3/Met_KHSS | Her3/Met_SSKH | Her3/Met_SSKHSS | Her3/Met_1C | Her3/Met_6C |
|---|---|---|---|---|---|
| Knobs-in-hole mutations | S354C:T366W/ Y349'C:T366'S: L368'A:Y407'V | T366W/ T366'S:L368'A: Y407'V | S354C:T366W/ Y349'C:T366'S: L368'A:Y407'V | S354C:T366W/ Y349'C:T366'S: L368'A:Y407'V | S354C:T366W/ Y349'C:T366'S: L368'A:Y407'V |
| Full length antibody backbone derived from | Her3 clone 29 (chimeric) | Her3 clone 29 (chimeric) | Her3 clone 29 (chimeric) | Her3 clone 29 (chimeric) | Her3 clone 29 (chimeric) |
| VHVLfragment derived from | cMet 5D5 (humanized) | cMet 5D5 (humanized) | cMet 5D5 (humanized) | cMet 5D5 (humanized) | cMet 5D5 (humanized) |
| Position of VH attached to antibody | C-terminus knob heavy chain | C-terminus knob heavy chain | C-terminus knob heavy chain | C-terminus knob heavy chain | C-terminus knob heavy chain |
| Position of VL attached to antibody | C-terminus hole heavy chain | C-terminus hole heavy chain | C-terminus hole heavy chain | C-terminus hole heavy chain | C-terminus hole heavy chain |
| Peptide connector | $(G_4S)_3$ | $(G_4S)_3$ | $(G_4S)_3$ | $(G_4S)_1$ | $(G_4S)_6$ |
| VHVL disulfide VH44/VL100 stabilized | – | + | + | – | – |

Figure 5:
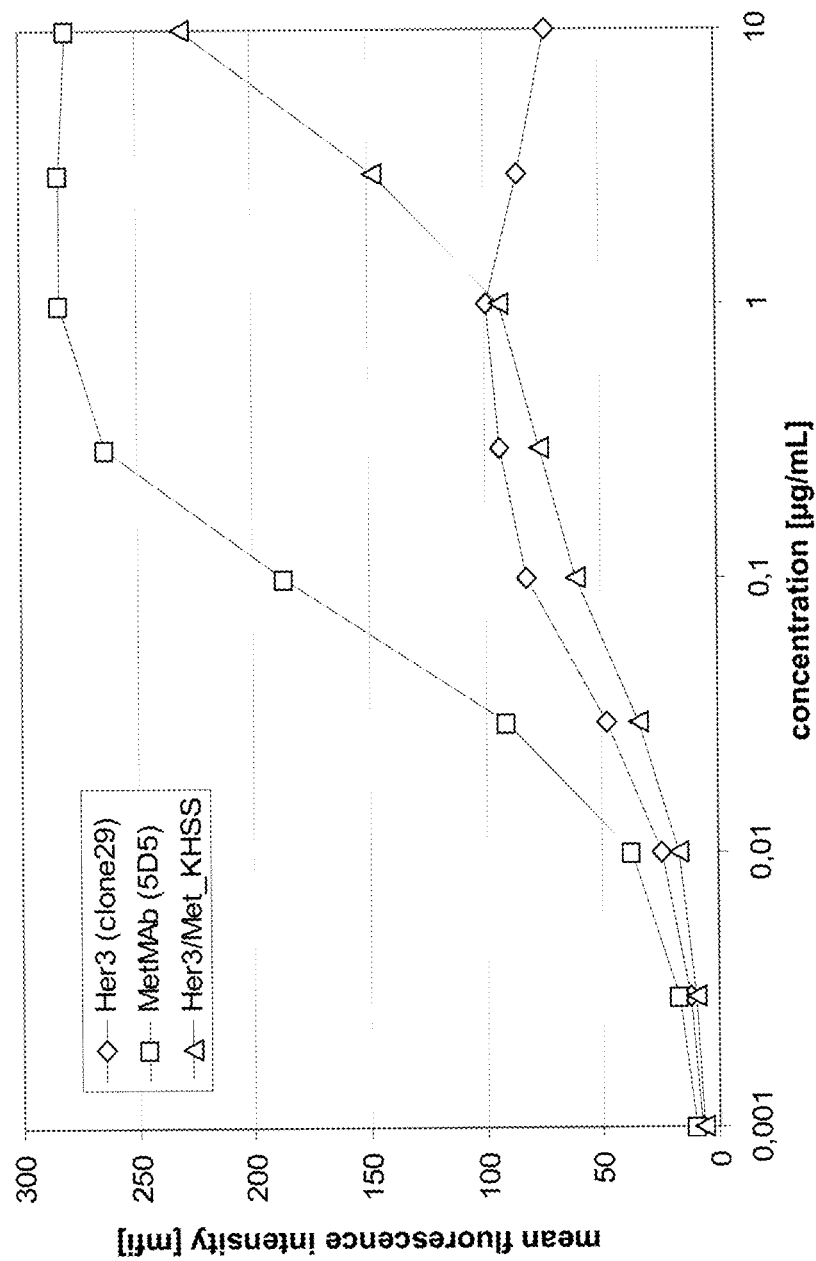
FIG. 5 Binding of bispecific antibodies to the cell surface of cancer cells

Example 1 (FIG. 5)

Binding of Bispecific Antibodies to the Cell Surface of Cancer Cells

The binding properties of the bispecific antibodies to their respective receptor on the cell surface was analyzed on A431 cancer cells in a flow cytometry based assay. Cells were incubated with the mono- or bispecific primary antibodies and binding of these antibodies to their cognate receptors was detected with a secondary antibody coupled to a fluorophore binding specifically to the Fc of the primary antibody. The mean fluorescence intensity of a dilution series of the primary antibodies was plotted against the concentration of the antibody to obtain a sigmoidal binding curve. Cell surface expression of c-Met and Her3 was validated by incubation with the bivalent 5D5 and Her3 clone 29 antibody only. The Her3/c-Met_KHSS antibody readily binds to the cell surface of A431. Under these experimental settings, the antibody can only bind via its Her3 part and consequently the mean fluorescence intensity does not exceed the staining for Her3 clone 29 alone.

Figure 6A:
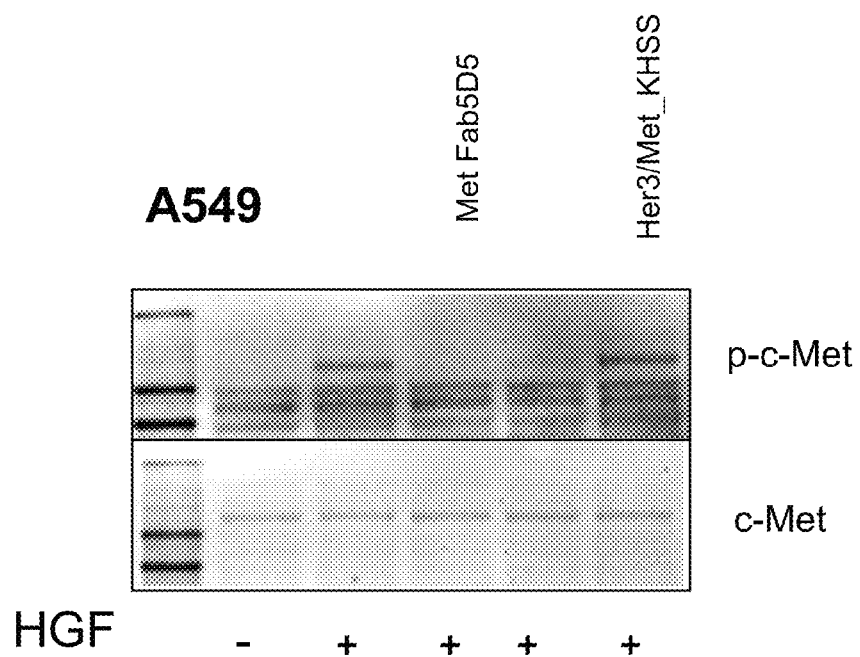
FIG. 6a) A549 cells, FIG. 6b) HT29 cells, and FIG. 6c) HT29 cells.
Figure 6B:
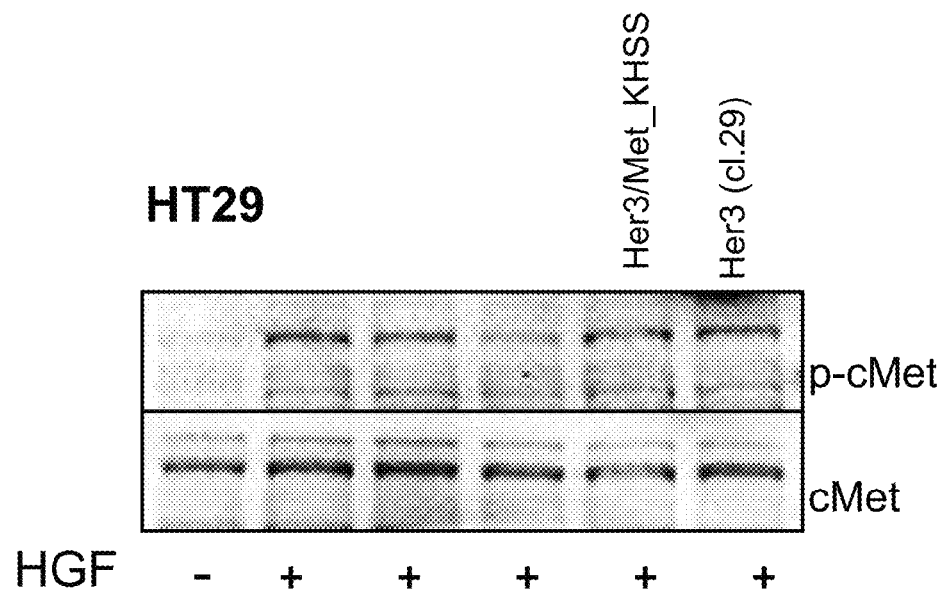
FIG. 6 Inhibition of HGF-induced c-Met receptor phosphorylation by bispecific Her3/c-Met antibody formats in different cell lines.
Figure 6C:
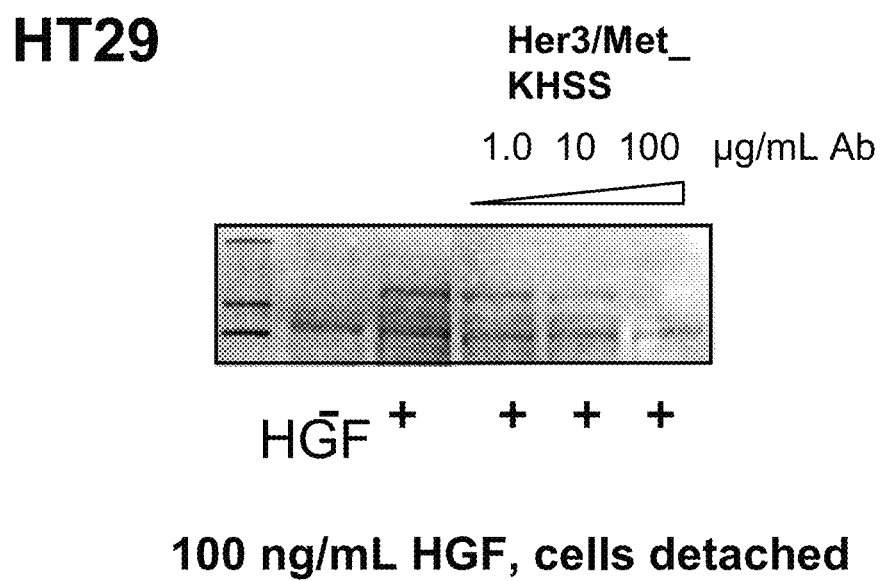

Example 2 (FIG. 6)

Inhibition of HGF-Induced c-Met Receptor Phosphorylation by Bispecific Her3/c-Met Antibody Formats To confirm functionality of the c-Met part in the bispecific antibodies a c-Met phosphorylation assay was performed. In this experiment A549 lung cancer cells or HT29 colorectal cancer cells were treated with the bispecific antibodies or control antibodies prior exposure to HGF. Cells were then lysed and phosphorylation of the c-Met receptor was examined. Both cell lines can be stimulated with HGF as can be observed by the occurrence of a phospho-c-Met specific band in the immunoblot.

Figure 7A:
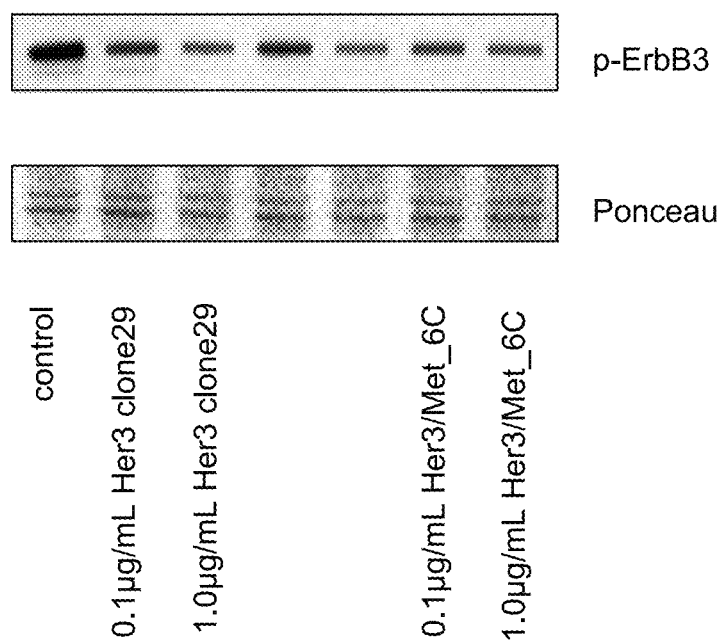
FIG. 7a) Phosphorylation of Her3 in MCF7 cells, and FIG. 7b) Inhibition of PhosphoHER3 at 0.1 µg/ml and 1 µg/ml.
Figure 7B:
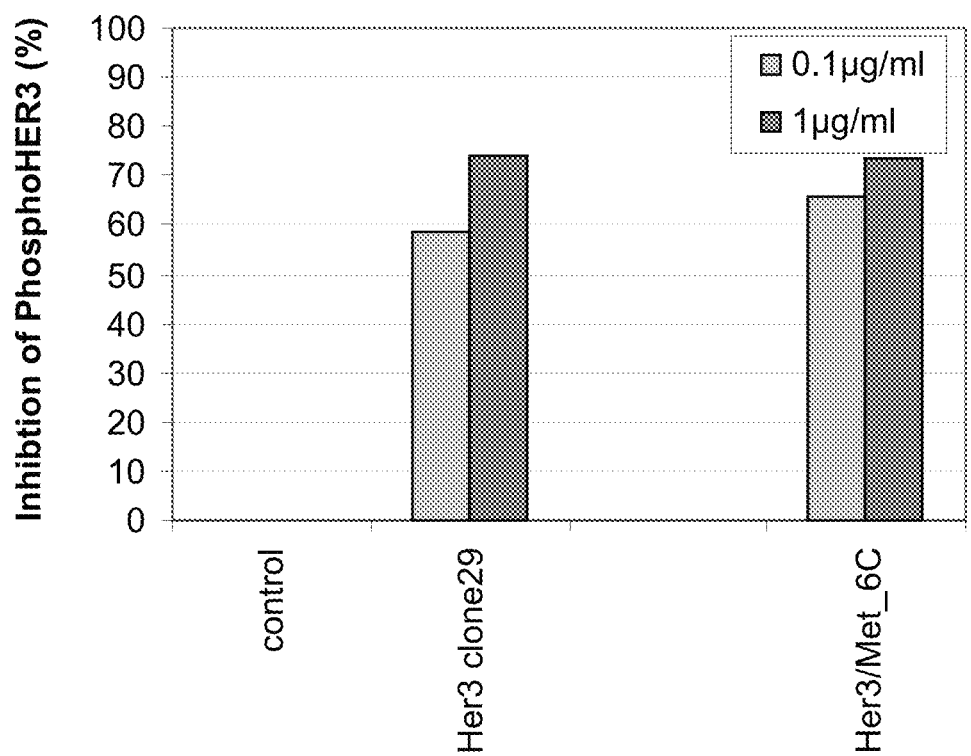
FIG. 7 Inhibition of HRG-induced Her3 receptor phosphorylation by bispecific Her3/c-Met antibody formats.

Example 3 (FIG. 7)

Inhibition of HRG-Induced Her3 Receptor Phosphorylation by Bispecific Her3/c-Met Antibody Formats To confirm functionality of the Her3 part in the bispecific antibodies a Her3 phosphorylation assay was performed. In this experiment MCF7 cells were treated with the bispecific antibodies or control antibodies prior exposure to HRG (Heregulin). Cells were then lysed and phosphorylation of the Her3 receptor was examined. Her3/c-Met_KHSS inhibit Her3 receptor phosphorylation to the same extent as the parental Her3 clone29 indicating that Her3 binding and functionality of the antibody are not compromised by the trivalent antibody format.

Figure 8:
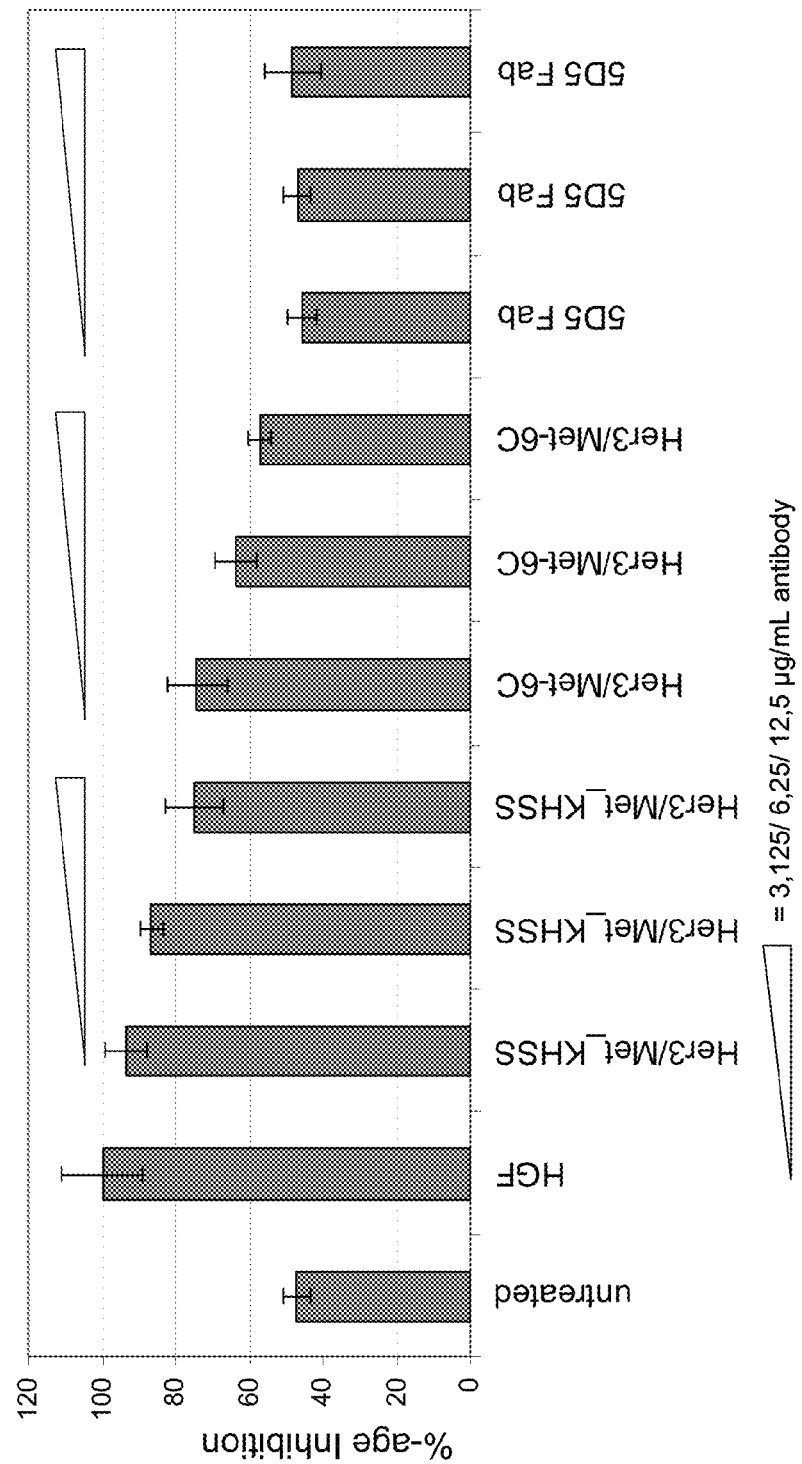
FIG. 8 Inhibition of HGF-induced HUVEC proliferation by bispecific Her3/c-Met antibody formats FIG. 9 Inhibition of proliferation in the cancer cell line A431 by bispecific Her3/c-Met antibody formats.

Example 4 (FIG. 8)

Inhibition of HGF-Induced HUVEC Proliferation by Bispecific Her3/c-Met Antibody Formats HUVEC proliferation assays were performed to demonstrate the mitogenic effect of HGF. Addition of HGF to HUVEC leads to a twofold increase in proliferation. Addition of human IgG control antibody in the same concentration range as the bispecific antibodies has no impact on cellular proliferation while the 5D5 Fab fragment inhibits HGF-induced proliferation. Titration of Her3/c-Met_KHSS demonstrate a weak inhibitory effect of the antibody (FIG. 8). The effect is more pronounced for the Her3/Met-6C antibody indicating that a longer connector improves efficacy of the antibody. This demonstrates the functionality of the c-Met component in the trivalent antibody format.

Figure 9:
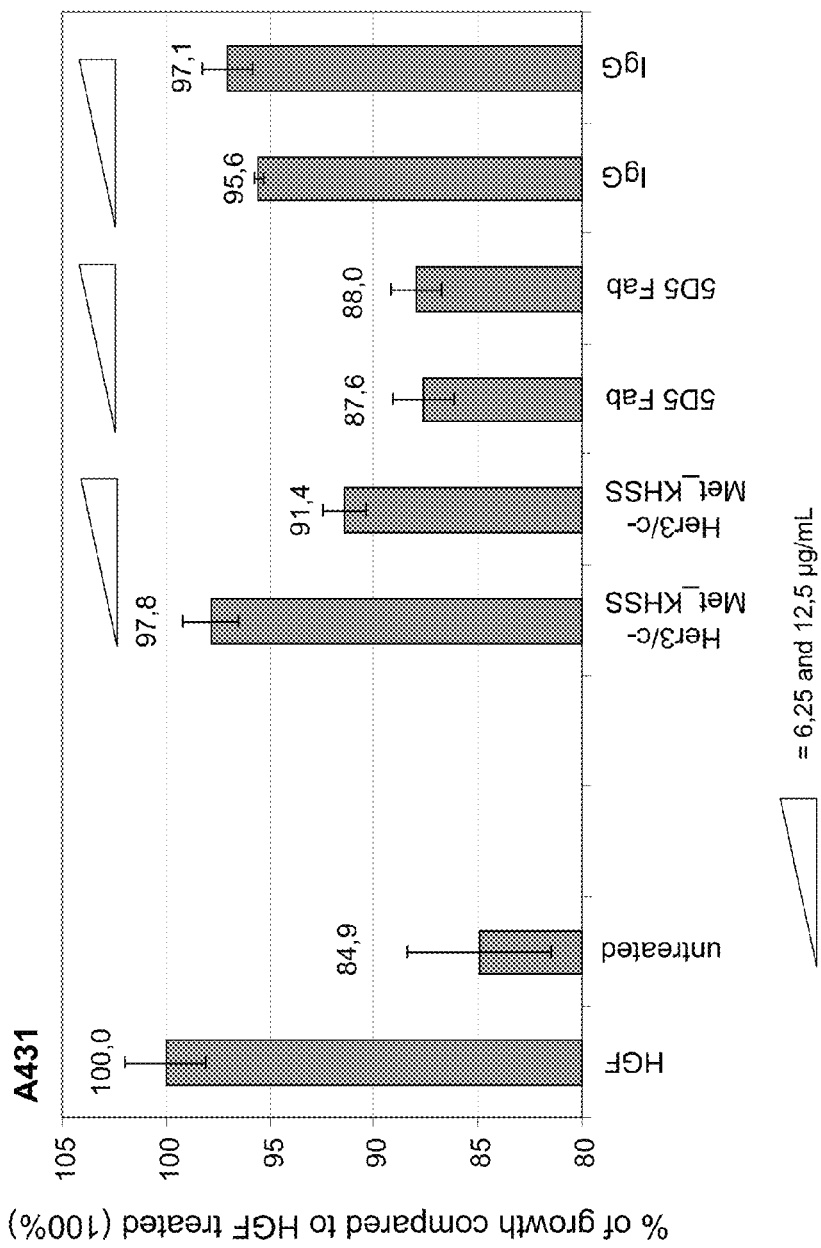

Example 5 (FIG. 9)

Inhibition of Proliferation in the Cancer Cell Line A431 by Bispecific Her3/c-Met Antibody Formats If A431 were seeded in serum reduced medium, addition of HGF induces apart from scattering a weak mitogenic effect. This was exploited to analyze the impact of Her3/c-Met_KHSS on HGF treated A431 proliferation. Indeed, the bispecific antibodies can largely inhibit the HGF-induced increase of proliferation (15%). A control human IgG1 antibody has no influence on HGF promoted A431 cell growth.

Figure 10:
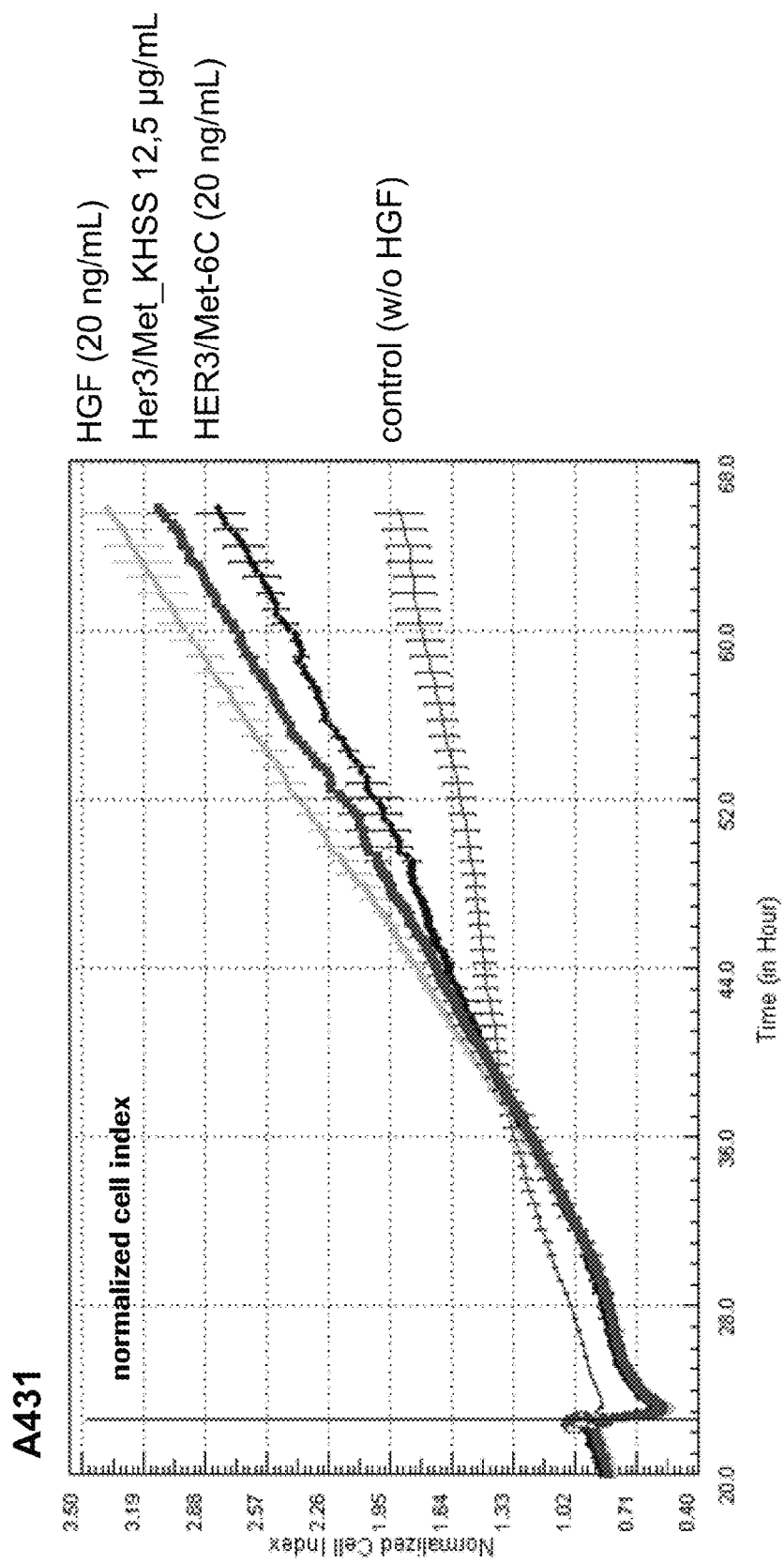
FIG. 10 Analysis of inhibition of HGF-induced cell-cell dissemination (scattering) in the cancer cell line A431 by bispecific Her3/c-Met antibody formats.

Example 6 (FIG. 10)

Analysis of Inhibition of HGF-Induced Cell-Cell Dissemination (Scattering) in the Cancer Cell Line A431 by Bispecific Her3/c-Met Antibody Formats HGF-induced scattering includes morphological changes of the cell, resulting in rounding of the cells, filopodia-like protrusions, spindle-like structures and a certain motility of the cells. The Real Time Cell Analyzer (Roche) measures the impedance of a given cell culture well and can therefore indirectly monitor changes in cellular morphology and proliferation. Addition of HGF to A431 and A549 cells resulted in changes of the impedance which was monitored as function of time. Her3/c-Met_KHSS and Her3/Met-6C inhibited HGF-induced scattering with Her3/Met-6C being more efficacious (20.7% and 43.7% scatter inhibition) (FIG. 10).

What is claimed is:

1. A trivalent, bispecific antibody comprising a) a full length IgG1 antibody that specifically binds to a first antigen wherein the full length antibody consists of two antibody heavy chains and two antibody light chains, wherein the CH3 domain of one heavy chain and the CH3 domain of the other heavy chain each meet at an interface which comprises an alteration in the original interface between the antibody CH3 domains, wherein i) in the CH3 domain of one heavy chain an amino acid residue is replaced with an amino acid residue having a larger side chain volume, thereby generating a protuberance within the interface of the CH3 domain of one heavy chain which is positionable in a cavity within the interface of the CH3 domain of the other heavy chain and wherein ii) in the CH3 domain of the other heavy chain an amino acid residue is replaced with an amino acid residue having a smaller side chain volume, thereby generating a cavity within the interface of the second CH3 domain within which a protuberance within the interface of the first CH3 domain is positionable;

b) a polypeptide consisting of
   ba) an antibody heavy chain variable domain (VH); or
   bb) an antibody heavy chain variable domain (VH) and an antibody constant domain 1 (CH1), wherein the N-terminus of the VH domain of the polypeptide is fused via a peptide connector to the C-terminus of one of the two heavy chains of the full length antibody;

c) a polypeptide consisting of
   ca) an antibody light chain variable domain (VL), or
   cb) an antibody light chain variable domain (VL) and an antibody light chain constant domain (CL);

wherein N-terminus of the VL domain of the polypeptide is fused via a peptide connector to the C-terminus of the other of the two heavy chains of the full length antibody;

wherein the antibody heavy chain variable domain (VH) of the polypeptide under b) and the antibody light chain variable domain (VL) of the polypeptide under c) together form an antigen-binding site specifically binding to a second antigen; and wherein the peptide connectors under b) and c) are peptides with a length between 5 and 50 amino acids.

2. The trivalent, bispecific antibody according to claim 1, wherein
   i) the amino acid residue having a larger side chain volume is selected from the group consisting of arginine (R), phenylalanine (F), tyrosine (Y), tryptophan (W); and
   ii) the amino acid residue having a smaller side chain volume is selected from the group consisting of alanine (A), serine (S), threonine (T), valine (V).

3. The trivalent, bispecific antibody according to claim 2, wherein
   both CH3 domains are further altered by the introduction of cysteine as an amino acid in each CH3 domain such that a disulfide bridge between both CH3 domains can be formed.

4. The trivalent, bispecific antibody according to claim 3, wherein
   the CH3 domain under i) comprises a T366W mutation; and
   the CH3 domain under ii) comprises T366S, L368A, and Y407V mutations.

5. The trivalent, bispecific antibody according to claim 4, wherein
   the CH3 domain under i) comprises Y349C and T366W mutations; and
   the CH3 domain under ii) comprises S354C, T366S, L368A, and Y407V mutations.

6. The trivalent, bispecific antibody according to claim 3, wherein
   the antibody heavy chain variable domain (VH) of the polypeptide under b) and the antibody light chain variable domain (VL) of the polypeptide under c) are linked and stabilized via a interchain disulfide bridge by introduction of a disulfide bond between the following positions:
   i) heavy chain variable domain position 44 to light chain variable domain position 100,
   ii) heavy chain variable domain position 105 to light chain variable domain position 43, or
   iii) heavy chain variable domain position 101 to light chain variable domain position 100.

7. The trivalent, bispecific antibody according to claim 6, wherein
   the antibody heavy chain variable domain (VH) of the polypeptide under b) and the antibody light chain variable domain (VL) of the polypeptide under c) are linked and stabilized via a interchain disulfide bridge by introduction of a disulfide bond between the following positions: i) heavy chain variable domain position 44 to light chain variable domain position 100.

8. The trivalent, bispecific antibody according to claim 5, wherein the peptide connectors under b) and c) are identical peptides with a length between 25 and 50 amino acids.

9. A pharmaceutical composition comprising a trivalent, bispecific antibody according to claim 1.

10. The trivalent, bispecific antibody according to claim 1, wherein the peptide connectors comprises Glycine (G) and Serine (S) residues.

11. The trivalent, bispecific antibody according to claim 10, wherein the peptide connector comprises GGGGS (SEQ ID NO:34) repeats.

* * * * *